(12) United States Patent
Matray et al.

(10) Patent No.: US 6,673,550 B2
(45) Date of Patent: *Jan. 6, 2004

(54) ELECTROPHORETIC TAG REAGENTS COMPRISING FLUORESCENT COMPOUNDS

(75) Inventors: Tracy Matray, San Lorenzo, CA (US); Vincent Hernandez, Brookdale, CA (US); Sharat Singh, San Jose, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 10/008,495

(22) Filed: Nov. 9, 2001

(65) Prior Publication Data

US 2002/0146726 A1 Oct. 10, 2002

Related U.S. Application Data

(63) Continuation-in-part of application No. 09/698,846, filed on Oct. 27, 2000, which is a continuation-in-part of application No. 09/602,586, filed on Jun. 21, 2000, now Pat. No. 6,514,700, which is a continuation-in-part of application No. 09/684,386, filed on Oct. 4, 2000, now abandoned, which is a continuation-in-part of application No. 09/561,579, filed on Apr. 28, 2000, which is a continuation-in-part of application No. 09/303,029, filed on Apr. 30, 1999, now Pat. No. 6,322,980.

(51) Int. Cl.⁷ .......................... C12Q 1/68; C12P 19/34; C07H 21/04; C07H 21/00
(52) U.S. Cl. .................. 435/6; 435/91.2; 536/24.3; 536/25.32
(58) Field of Search ................... 435/6, 91.2; 536/24.3, 536/25.32

(56) References Cited

U.S. PATENT DOCUMENTS

| | | |
|---|---|---|
| 4,274,240 A | 6/1981 | Soum |
| 4,331,590 A | 5/1982 | Bocuslaski et al. .......... 260/112 |
| 4,650,750 A | 3/1987 | Giese ............................. 435/7 |
| 4,675,300 A | 6/1987 | Zare et al. |
| 4,709,016 A | 11/1987 | Giese ........................... 530/389 |
| 4,780,421 A | 10/1988 | Kameda ....................... 436/518 |
| 5,324,401 A | 6/1994 | Yeung et al. |
| 5,340,716 A | 8/1994 | Ullman ........................... 435/6 |
| 5,360,819 A | 11/1994 | Giese ........................... 514/538 |
| 5,470,705 A | 11/1995 | Grossman et al. |
| 5,470,967 A | 11/1995 | Huie et al. |
| 5,516,636 A | 5/1996 | McCapra ....................... 435/6 |
| 5,516,931 A | 5/1996 | Giese ............................ 560/59 |
| 5,536,834 A | 7/1996 | Singh et al. |
| 5,552,028 A | 9/1996 | Madabhushi et al. |
| 5,560,811 A | 10/1996 | Briggs et al. |
| 5,565,324 A | 10/1996 | Still et al. |
| 5,573,906 A | 11/1996 | Bannwarth et al. |
| 5,580,732 A | 12/1996 | Grossman et al. |
| 5,604,104 A | 2/1997 | Giese ........................... 435/7.1 |
| 5,610,020 A | 3/1997 | Giese ........................... 435/7.1 |
| 5,622,929 A | 4/1997 | Willner ......................... 514/34 |
| 5,624,800 A | 4/1997 | Grossman et al. |
| 5,650,270 A | 7/1997 | Giese ............................. 435/6 |
| 5,703,222 A | 12/1997 | Grossman et al. |
| 5,709,994 A | 1/1998 | Pease ............................. 435/4 |
| 5,719,028 A | 2/1998 | Dahlberg et al. |
| 5,721,099 A | 2/1998 | Still et al. |
| 5,723,591 A | 3/1998 | Livak et al. |
| 5,756,726 A | 5/1998 | Hemmi et al. |
| 5,789,172 A | 8/1998 | Still et al. |
| 5,807,675 A | 9/1998 | Davalian ........................ 435/6 |
| 5,811,239 A | 9/1998 | Frayne |
| 5,843,655 A | * 12/1998 | McGall ......................... 435/6 |
| 5,843,666 A | 12/1998 | Akhavan-Tafti et al. |
| 5,846,839 A | 12/1998 | Gallop ......................... 436/518 |
| 5,874,213 A | 2/1999 | Cummins et al. |
| 5,876,930 A | 3/1999 | Livak et al. |
| 5,989,871 A | 11/1999 | Grossman et al. |
| 5,998,140 A | 12/1999 | Dervan et al. |
| 6,001,579 A | 12/1999 | Still et al. |
| 6,027,890 A | 2/2000 | Ness ............................. 435/6 |
| 6,045,676 A | 4/2000 | Mathies et al. |
| 6,090,947 A | 7/2000 | Dervan et al. |
| 6,251,581 B1 | * 6/2001 | Ullman et al. ................. 435/4 |
| 6,312,893 B1 | 11/2001 | Van Ness ...................... 435/6 |
| 6,368,874 B1 | 4/2002 | Gallop ......................... 436/518 |

FOREIGN PATENT DOCUMENTS

| | | |
|---|---|---|
| WO | WO 93/06121 | 4/1993 |
| WO | WO 96/24061 | 8/1996 |
| WO | WO 97/28275 | 8/1997 |
| WO | WO 98/01533 | 1/1998 |
| WO | WO 99/13108 | 3/1999 |
| WO | WO 99/42838 | 8/1999 |
| WO | WO 99/64519 | 12/1999 |
| WO | WO 00/56925 | 9/2000 |
| WO | WO 00/66607 | 11/2000 |

OTHER PUBLICATIONS

Giese Trends in analytical chemistry, 1993, vol. 2(7). p. 165–167.*

Adam, W. and Liu, J.–C., "Photooxygenation (Singlet Oxygen) of Tetrathioethylenes", *J. Am. Chem. Soc.* 94:1206–1209 (1972).

(List continued on next page.)

*Primary Examiner*—Ethan Whisenant
*Assistant Examiner*—Joyce Tung
(74) *Attorney, Agent, or Firm*—Stephen C. Macevicz

(57) ABSTRACT

Electrophoretic probes comprising fluorescent compounds as detection groups and mobility modifiers are disclosed for the multiplexed detection of the binding of, or interaction between, one or more ligands and target antiligands are provided. In one embodiment, detection involves the release of identifying tags as a consequence of target recognition. Target antiligands are contacted with a set of e-tag probes and the contacted antiligands are treated with a selected cleaving agent resulting in a mixture of e-tag reporters. Typically, uncleaved or partially cleaved e-tag probes are removed and the mixture of e-tag reporters is separated by any technique that provides for separation by mass or mass to charge ratio and the like and detected to provide for target identification.

20 Claims, 7 Drawing Sheets

OTHER PUBLICATIONS

Adam, W. et al., "Photooxygenation of Vinyl Sulfides: Substituent Effects on the [2+] Cycloaddition versus Schenck Ene Reaction Modes" *Tetrahedron Letters* 36(43):7853–7854 (1995).

Ando, W., et al., "Singlet Oxygen Reaction–II alkylthiosubstituted ethylene" *Tetrahedron Letters* 29:1507–1513 (1973).

Ando, W., et al., "Singlet Oxygen Reaction. III. 'Solvent and Temperature Effects' on the Photosensitized Oxygenation of Vinyl Sulfides and Vinyl Ethers" *J. Am. Chem. Soc.* 96:6766–6768 (1974).

Ando, W., et al., "Singlet Oxygen Reaction. IV. Photooxygenation of Enamines Involving a Two–Step Cleavage of a 1,2–Dioxetane Intermediate" *J. Am. Chem. Soc.* 97:5028–5029 (1975).

Ando, W., et al., "Singlet Oxygen Reaction V. Ring Size Effects on the Decomposition of Sulfur Substituted 1,2–Dioxetane" *Tetrahedron Letters* 47:4127–4130 (1975).

Brenner, S. and Lerner, R.A., "Encoded combinatorial chemistry" *Proc. Natl. Acad. Sci. USA* 89:5381–5383 (1992).

Hacia, J.G., et al., "Detection of heterozygous mutations in BRCA1 using high density ologonucleotide arrays and two–colour fluorescence analysis" *Nature Genetics.* 14:441–447 (1996).

Haff, L.A. and Smirnov, I.P., "Multiplex genotyping of PCR products with MassTag–labeled primers" *Nucleic Acids Res.* 25(18):3749–3750 (1997).

Lee, L.G., et al., "Allelic discrimination by nick–translation PCR with fluorogenic probes" *Nucleic Acids Research* 21(16):3761–3766 (1993).

Marino, M.A., et al., et al., "Characterization of mitochondrial DNA using low–stringency single specific primer amplification analyzed by laser fluorescence–capillary electrophoresis" *Electrophoresis* 17:1499–1504 (1996).

Matthews, J.A. and Kricka, L.J., "Analytical Strategies for the Use of DNA Probes" *Anal. Biochem.* 169: 1–25 (1988).

Pastinen, T., et al., "Multiplex, fluorescent, solid–phaser minisequencing for efficient screening of DNA sequence variation" *Clinical Chemistry* 42(9):1391–1397 (1996).

Ross, P.L., et al., "Discrimination of Single–Nucleotide Polymorphisms in Human DNA Using Peptide Nucleic Acid Probes Detected by MADI–TOF Mass Spectrometry" *Anal. Chem.* 69:4197–4202 (1997).

Still, W.C., "Discovery of Sequence–Selective Peptide Binding by Synthetic Receptors Using Encoded Combinatorial Libraries" *Accounts of Chem. Res.* 29:155–163 (1996).

Ullman, E.F., et al., "Luminescent oxygen channeling immunoassay: Measurement of particle binding kinetics by chemiluminescence" *Proc. Natl. Acad. Sci.,* 91:5426–5430 (1994).

Wang, D.G., et al., "Large–Scale Identification, Mapping, and Genotyping of Single–Nucleotide Polymorphisms in the Human Genome" *Science* 280(5366):1077–1082 (1997).

Wasserman, H.H. and Terao, S., "Enamine–singlet oxygen oxygen reactions. α–diketones from intermediate amino dioxetanes" *Tetrahedron Letters* 21:1735–1738 (1975).

Wetmur, J.G., "DNA Probes: Applications of the Principles of Nucleic Acid Hybridization" *Critical Rev. in Biochem. and Molecular Biol.* 26(3/4):227–259 (1991).

White, T.J., "The future of PCR technology: diversification of technologies and applications" *Trends in Biotechnology* 14:478–483 (1996).

Woolley, A.T., et al., "Functional Integration of PCR Amplification and Capillary Electrophoresis in a Microfabricated DNA Analysis Device", *Anal. Chem.* 68:4081–4086 (1996).

Zalika, K.A., et al., "Mechanisms of 1,2–dioxetane decomposition: the role of electron transfer" *Photochem. Photobiol.* 30:35–44 (1979).

Houghton, R.A. et al., "Human βEndorphin: Synthesis and Characterization of Analogs Iodinated and tritiated at Tryosine Residues 1 and 27", *Int. J. Peptide Protein Res.,* 16:311–320, 1980.

Marglin, A et al., "Chemical Synthesis of Peptides and Proteins", *Ann. Rev. Biochem.*, 39 841–866, 1970.

Merrifield, R.B., "Solid Phase Peptide Synthesis I. The Synthesis of a Tetrapeptide", *J. Am. Chem. Soc.*, 85:2199–2154, 1980.

Ando, W. et al., "Photosensitized Oxygenation of Vinylic Sulphides", *J.C.S. Chem. Comm.*, 477–478, 1972.

Holland, P.M. et al., "Detection of specific polymerase chain reaction product by utilizing the 5'→3' exonuclease activity of *Thermus aquaticus* DNA polymerase", *Proc. Natl. Acad. Sci. USA*, vol. 88, pp. 7276–7280, Aug. 1991.

\* cited by examiner

AMD 007
MASS: 432
EX: 503
EM: 536

AMD 008
MASS: 426
EX: 500
EM: 526

AMD 009
MASS: 410
EX: 502
EM: 521

AMD 012
MASS: 476
EX: ND
EM: ND

AMD-S 001
MASS: 472
EX: 520
EM: 540
RQY: 1.0

AMD-S 002
MASS: 540
EX: 535
EM: 554
RQY: 1.0

ELECTROPHORETIC TAG REAGENTS COMPRISING FLUORESCENT COMPOUNDS

CROSS-REFERENCE TO RELATED APPLICATIONS

This application is a continuation-in-part (CIP) of Ser. No. 09/698,846, filed Oct. 27, 2000, which is a CIP of Ser. No. 09/602,586, filed Jun. 21, 2000 now U.S. Pat. No. 6,514,700, which, with Ser. No. 09/684,386 filed Oct. 4, 2000 now abandoned are CIP's of Ser. No. 09/561,579, filed Apr. 28, 2000, which is a CIP of Ser. No. 09/303,029, filed Apr. 30, 1999 now U.S. Pat. No. 6,322,980, all of which are incorporated herein by reference in their entirety.

FIELD OF THE INVENTION

The present invention relates to probes comprising fluorescent compounds. The present compositions may be employed in the detection and quantitation of analytes such as polypeptides, polynucleotides, hormones and drugs. In particular, the invention pertains to fluorescent compounds and their use as detection groups in electrophoretic probes.

BACKGROUND OF THE INVENTION

The need to determine many analytes (for example multiple pathogens or multiple genes or multiple genetic variants) in blood or other biological fluids has become increasingly apparent in many branches of medicine. Most multi-analyte assays, such as multiplexed assays that detect, e.g., multiple nucleic acid sequences, involve multiple steps, have poor sensitivity, a limited dynamic range (typically on the order of 2 to 100-fold differences and some require sophisticated instrumentation.

Fluorescent compounds are widely used as labels in a variety of diagnostic procedures. Fluorescent compounds are linked to other entities to form probes that are used to assay for a wide variety of materials of interest. In some applications it is important that fluorescent compounds employed as labels have different spectral properties. Such properties include wavelength of excitation, wavelength of emission, quantum yields, Stokes shift, and so forth.

BRIEF DESCRIPTION OF THE RELATED ART

U.S. Pat. No. 6,008,379 discloses aromatic substituted xanthene dyes.

U.S. Pat. No. 6,080,852 discusses 4,7-dichlororhodamine dyes.

Unsymmetrical fluorescein derivatives are disclosed in U.S. Pat. No. 4,439,356.

Xanthene dyes having a fused (C) benzo ring are discussed in U.S. Pat. No. 4,945,171.

4,7-Dichlorofluorescein dyes as molecular probes are discussed in WO 94/05688.

U.S. Pat. No. 4,351,760 discloses alkyl substituted fluorescent compounds and polyamino acid conjugates.

U.S. Pat. No. 4,318,846 discusses ether substituted fluorescein polyamino acid compounds as fluorescers and quenchers. PCT WO 97/39064 discloses fluorinated xanthene derivatives.

U.S. Pat. No. 5,807,682 describes probe compositions for detecting a plurality of nucleic acid targets.

SUMMARY OF THE INVENTION

In one embodiment the present invention is directed to electrophoretic tag probes, and sets of such probes, wherein a probe comprises a releasable portion that is separately detectable on the basis of mobility and a detectable moiety that is a compound of the formula:

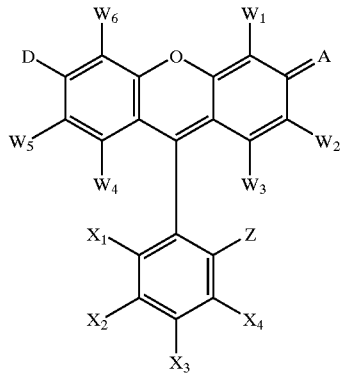

wherein:
Z is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, phosphorus containing species such as, e.g., phosphate, phosphite, and the like, polymer chains of from about 2 to about 500, preferably, about 5 to about 100 monomer units such as, e.g., nucleotides, amino acids, amides, esters, ethers, amines, and so forth, A is O, $N^+(R^1)(R^2)$ wherein $R^1$ and $R^2$ are independently H, lower alkyl, substituted lower alkyl, and the like, D is OH, $OR^3$ wherein $R^3$ is lower alkyl, substituted lower alkyl, aryl, substituted aryl, and the like, $N(R^1)(R^2)$ wherein $R^1$ and $R^2$ are independently H, lower alkyl, substituted lower alkyl, $W^1$, $W^2$, $W^3$, $W^4$, $W^5$ and $W^6$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and so forth, $X^1$–$X^4$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and so forth, wherein $W^2$ and $W^3$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^4$ and $W^5$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, The electrophoretic probes may be used in methods for simultaneously determining multiple analytes in a sample suspected of containing the analytes. In the method a combination is provided comprising the sample and an electrophoretic tag probe comprising a releasable portion that is separately detectable on the basis of mobility and the presence therein of a fluorescent compound in accordance with the invention. The electrophoretic tag probe, or e-tag probe, is involved in a binding event that is related to the presence of the analyte in the sample. The combination is treated with reagents under conditions sufficient to release the releasable portion, forming an e-tag reporter. The presence and/or amount of the released e-tag reporter is detected and is related to the presence and/or amount of the analyte in the sample.

DESCRIPTION OF THE SPECIFIC EMBODIMENTS

Figure 1A:
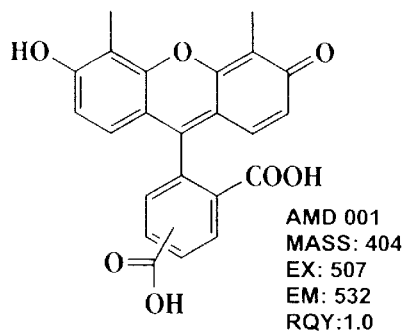
FIG. 1 depicts fluorescent compounds employed in the present invention.
Figure 1A:
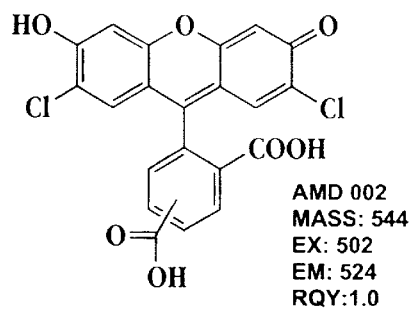
Figure 1A:
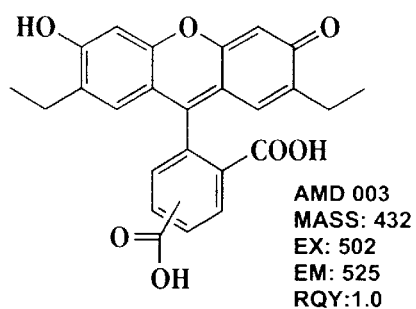
Figure 1A:
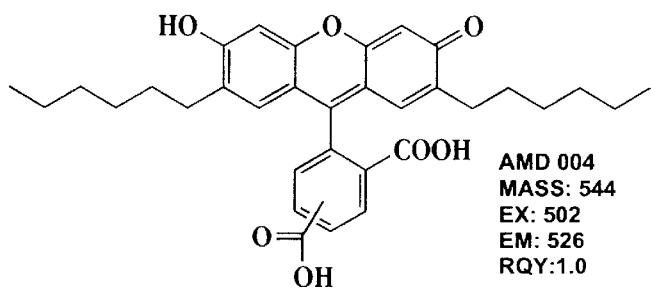
Figure 1A:
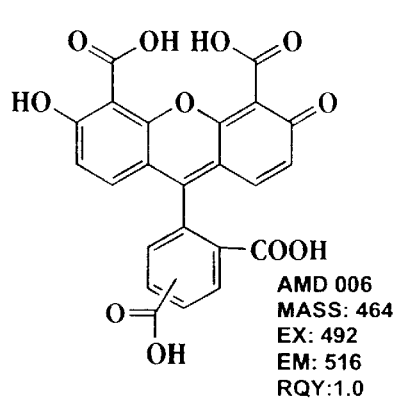
Figure 1A:
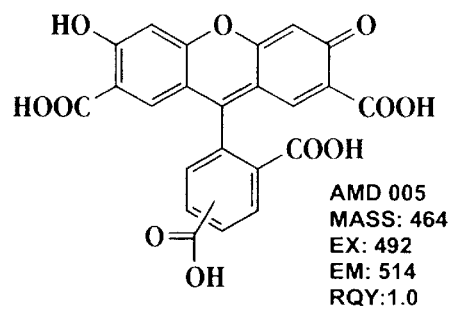
Figure 1B:
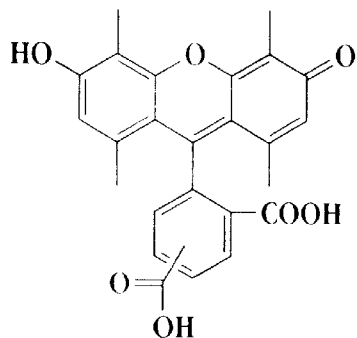
Figure 1B:
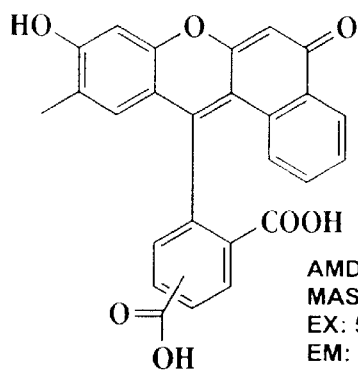
Figure 1B:
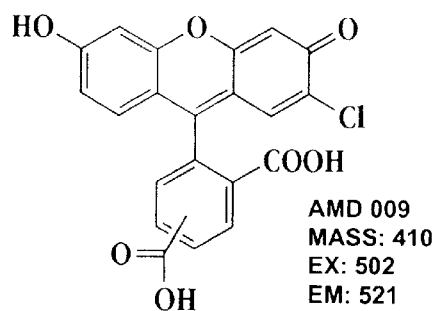
Figure 1B:
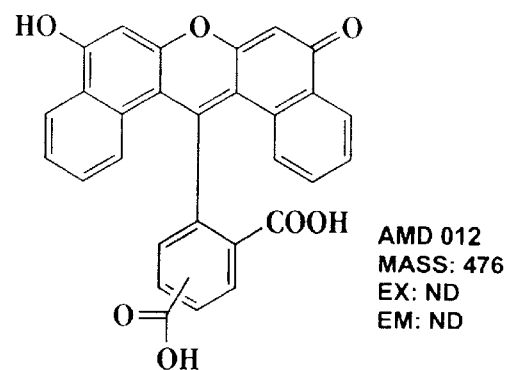
Figure 1B:
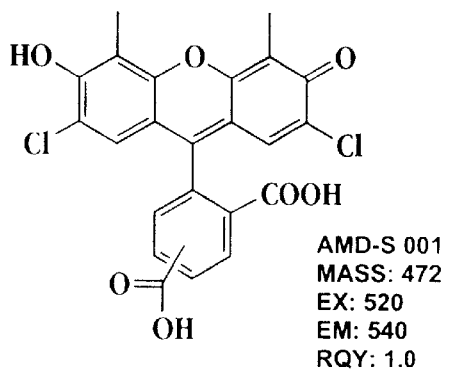
Figure 1B:
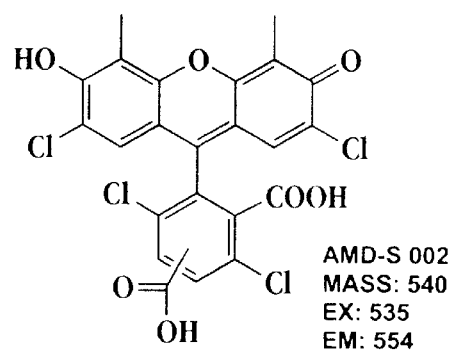

Methods and compounds are provided for multiplexed determinations, where the compounds can be linked to binding compounds for detection of reciprocal binding compounds in a sample. The methods are distinguished by having a plurality of binding events in a single vessel using a mixture of differentially eTag reporter conjugated binding compounds, the release of identifying eTag reporter of those binding compounds bound to their target compounds in the same vessel, and the detection of the released identifying tags by separation of the tags in a single run. The eTag reporter are distinguished by having one or more physical characteristics that allow them to be separated and detected.

The method employs a mixture of binding compounds bound to eTag reporters, where each eTag reporter has a characteristic that allows it to be uniquely detected in a single separation run. The method involves combining the eTag reporter conjugated binding compound with a sample to determine the presence of a plurality of targets under conditions where the binding compounds bind to any reciprocal binding partners to form a binding complex. After sufficient time for binding to occur, the eTag reporters can be released from binding complexes in the same vessel. Various techniques are employed depending upon the nature of the binding compounds for releasing the eTag reporters bound to the complex. The released eTag reporters are then separated and identified by their differentiable characteristics free of interference from the eTag reporters still bound to the binding compound. The techniques for differentiating between eTag reporters bound to a complex and not bound to a complex, include enzymatic reactions that require the complex to exist for cleavage to occur, modification by using ligand/receptor binding, where the ligand is part of the binding compound, so that after cleavage, eTag reporter still bound to the binding compound is modified, dual binding to the target resulting in release of the eTag reporter, where optionally eTag reporter bound to the binding compound is modified, and the like.

One set of eTag reporters are distinguished by differences, which include mass as a characteristic. These eTag reporters do not rely on differentiation based on oligonucleotides of 2 or more, usually 3 or more nucleotides, but rather on organic chemical building blocks that are conveniently combined together to provide for large numbers of differentiable compounds. Therefore, while the original eTag reporter or eTag reporter conjugated to the binding compound can have 2 or more nucleotides, when release from the binding compound, the released eTag reporter will have not more than 3, usually not more than 2 nucleotides. Of particular interest are eTag reporters that are characterized by differences in their mass/charge ratio. These compounds are distinguished by having differences in mobility and are characterized by having regions, which serve as (1) a cleavable linking region; (2) a mass-modifying region; (3) a charge-modifying region: and (4) a detectable region, where the regions may be separate and distinct or combined, there being at least two distinct regions that provide for the differentiation. These eTag reporters may be combined in kits and assays with compounds having all of the regions within a single region to further expand the number of different compounds used as eTag reporters in a multiplexed determination. These compounds find use with other compounds where the different regions are present in the same moiety, for example one to two regions, where the charge-modifying region may also be the detectable region or the mass-modifying region. By having a plurality of compounds that can serve as identifying molecules, mixtures of target compounds can be assayed in a single vessel. By using protocols that result in the release of eTag™ reporters from the binding compound that are identifiable due to differences in mobility, the analysis is greatly simplified, since the eTag reporters will be substantially free of interfering materials and their differences in mobility will allow for accurate detection and quantitation.

The eTag reporters will vary depending upon the method of detection. Groups of at least 10 eTag reporters bound to 10 different binding compounds will be used in the determinations. The eTag reporters will be characterized by being cleavable from the binding compound in the same vessel by the same cleavage mechanism, having a shared characteristic that permits separation and individual detection, being compatible with the determination method and being in the molecular weight range of about 30 to 3000 dal, usually in the molecular weight range of about 35 to 1500 dal. The variation may be mass using a mass spectrometer, where a magnetic field is used for separation, mass/charge ratio using electrokinesis, where an electric field is used for separation, which may also include sieving and/or adsorbing polymers, adsorption, using chromatography, e.g gas chromatography, high pressure liquid chromatography, where polar and van der Waal interactions are used for separation, etc.

Proteomics has home to the fore, where one is interested in cellular expression during metabolism, mitosis, meiosis, in response to an external stimulus, e.g. drug, virus, change in physical or chemical condition, involving excess or deficient nutrients and cofactors, stress, aging, presence of particular strains of an organism and identifying the organism and strain, multiple drug resistance, and the like. It is necessary to have a means for identifying a large number of proteins in a single sample, as well as providing some quantitation of the different proteins being detected. In one assay one may use binding proteins specific for the target proteins. One group of binding proteins is bound to a support, such as a vessel or channel wall, particles, magnetic or non-magnetic, e.g. latex particles, dextrose, sepharose, cellulose, etc. where the support permits sequestering the target proteins to the support. Most commonly, antibodies, particularly monoclonal antibodies rather than antisera, will be used, although the latter may also find use. In some situations other receptors may find use, such as lectins, enzymes, surface membrane proteins, etc. and in some situations, ligands for the proteins may be employed. The reciprocal-binding members, receptors and ligands, may be bound to the support through covalent or non-covalent bonding. Activated surfaces find use, where the surface has an active functional group that will react with the reciprocal-binding member to provide for stable binding to the surface, e.g. silyl chloride modified glass, cyanogen bromide modified polysaccharides, etc. Proteins bind tightly to some plastic surfaces, so that no covalent bonding is required. Ligands have or can be provided with active functional groups for bonding to the surface. If desired the binding to the surface can be accomplished in two steps by bonding a ligand to the reciprocal binding member and binding a ligand binding member to the support, for example, biotin as the ligand and strept/avidin as the ligand binding member, or one may have anti-Ig bound to the surface to bind to antibodies bound to the target protein. In addition, where a change in environment is localized, one may have a large concentration of a counteracting agent, e.g. a large amount of buffer at pH 7, for example, $\geq 200$ mM phosphate, where ammonia is produced that creates a localized basic environment.

The sample is combined with the reciprocal binding member, which may be bound to the support or subsequently bound to the support. After washing away the other components of the mixture, receptor for the target protein labeled with eTag reporter molecules specific for the particular receptor are added to the bound target protein, so as to become bound to the support through the target protein. One or more eTag reporter molecules will be bound to the receptor, usually not more than about 20, frequently not more than about 10. The number will be limited by the degree of loss of the binding affinity as the number of eTag reporter molecules is increased. Normally, the support bound receptor and the eTag reporter labeled receptor will bind to different epitopes of the target protein, although in some situations where the target has a plurality of the same epitope, the receptors may be specific for the same epitope. After washing away all eTag reporter labeled receptor that is not specifically bound to the target protein(s), the eTag reporter molecules are released and assayed.

Where the target permits binding of two reciprocal binding members or where an additional reagent is provided which permits this event, one can use determinations involving "channeling" or energy transfer. See, for example, U.S. Pat. Nos. 5,843,666 and 5,573,906. There are numerous methodologies involving channeling in the literature, where for the most part, the channeling was involved in producing a directly detectable signal, usually a change in absorption or emission of light. Channeling involves having two reagents, where the first reagent, when in proximity to the second reagent, produces a detectable signal. For the eTag reporter, the detectable signal is the release of the eTag reporter from the binding component. The release will usually be a function of the production of a short-lived entity, such as a chemical species or a photoactivated excited species, but may be the result of changing the local environment as compared to the bulk solution. So far as the chemical species, illustrative species include singlet oxygen, hydrogen peroxide, NADH, and hydroxyl radicals. Two entities are employed that have reciprocal binding members that bind to the same target moiety. One of the entities generates an active species. The other entity has a susceptible functionality that interacts with the active species resulting in release of the eTag reporter or responds to the changed local environment to release the eTag reporter. Either the active species is short lived, so that it will not create significant background because beyond its vicinity, the active species becomes inactive or a scavenger is employed that efficiently scavenges the active species, so that it is not available to react with the susceptible functionality that is not bound to the target.

Generators of reactive species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH. One cleavable link can be based on the oxidation of sulfur or selenium, where a thioether, sulfoxide, or selenium analog thereof, is present at the $\alpha$- or $\beta$-position in relation to an activating group, which makes the hydrogen $\alpha$ to the activating group acidic and capable of being removed by base, so as to release the oxidized functionality to which is attached the eTag reporter or to be subject to oxidation with release of the eTag reporter. Alternatively, one may use metal chelates that are stable at one oxidation state and unstable at another oxidation state. Other compounds include $\alpha$-substituted methylquinones, which have an eTag reporter bonded through a leaving group, such as sulfonyl, oxy, amino, etc.

By using a heterogeneous system, a first agent for causing cleavage may be bound to a surface to provide an environment for release of the eTag reporter when bound to the surface. Where a second agent is required to cause the release of the eTag reporter, the second agent is added after sufficient time for the eTag reporter conjugated binding compound to become bound to the surface. Where the target is a nucleic acid, the nucleic acid may be bound to the first agent containing surface by having ssDNA binding proteins bound to the surface or other convenient means known in the art. Once the target is bound to the surface, the eTag reporter conjugated oligonucleotides homologous the target nucleic acid sequences are added, followed by the second agent. With ligands and proteins, one can have receptors, which bind at one site, on the surface and eTag reporter binding compounds that bind at a different site forming what is referred to in the art as a "sandwich."

For singlet oxygen, one may use various sensitizers, such as squarate derivatives. See, for example, Ullman, et al., Proc. Natl. Acad. Sci. USA 91, 5426–5430 (1994). Examples of combinations that find use in this invention may be found in U.S. Pat. Nos. 5,536,498; 5,536,834; references cited therein; H. H. Wasserman and R. W. Murray. Singlet Oxygen. Academic Press, New York (1979); A. L. Baumstark, Singlet Oxygen, Vol. 2, CRC Press Inc., Boca Raton, Fla. 1983. Other cleavage mechanisms may be found in WO99/645 19; WO99/13 108; WO98/01533 and WO97/28275.

Singlet oxygen reacts with a wide variety of double bonds, with cleavage of the double bond to an oxo group with separation of the eTag reporter. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 750° C., reaction with acid or base, or photolytically in the absence or presence of a sensitizer. Numerous articles describe a variety of compounds that can be decomposed with singlet oxygen, where the articles are frequently interested in light emission, so that the compounds have more complicated structures than are required for the subject purposes, where only cleavage is required for release of the eTag reporter from the binding compound. Therefore, for the most part, synthetic convenience. stability under the conditions of the linking to the binding compound and conditions of the binding, and efficiency of release will be the primary factors in selecting a particular structure.

Articles of interest which are illustrative of a much larger literature include: Adam and Liu, J. Amer. Chem. Soc. 94, 1206–1209, 1972, Ando, et al., J. C. S. Chem. Comm. 1972, 477–8, Ando, et al., Tetrahedron 29, 1507–13, 1973, Ando, et al., J. Amer. Chem. Soc. 96, 6766–8, 1974, Ando and Migita, ibid 97, 5028–9, 1975, Wasserman and Terao, Tetra. Lett. 21, 1735–38, 1975, Ando and Watanabe, ibid 47, 4127–30, 1975, Zaklika, et al., Photochemistsry and Photobiology 30, 35–44, 1979, and Adam, et al., Tetra. Lett. 36, 7853–4, 1995. See also, U.S. Pat. No. 5,756,726.

The formation of dioxetanes is obtained by the reaction of singlet oxygen with an activated olefin substituted with an eTag reporter at one carbon atom and the binding compound at the other carbon atom of the olefin. See, for example, U.S. Pat. No. 5,807,675. These compounds may be depicted by the following formula:

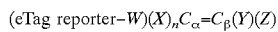

wherein:

W may be a bond, a heteroatom, e.g. O, S, N, P, M (intending a metal that forms a stable covalent bond), or a functionality, such as carbonyl, imino, etc., and may be bonded to X or $C_\alpha$;

at least one X will be aliphatic, aromatic, alicyclic or heterocyclic and bonded to $C_\alpha$ through a hetero atom, e.g. N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to $C_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to $C_\beta$ or through a heteroatom, as described above;

n is 1 or 2, depending upon whether the eTag reporter is bonded to $C_\alpha$, or X;

wherein one of Y and Z will have a functionality for binding to the binding member or be bound to the binding member.

While not depicted in the formula, one may have a plurality of eTag reporters in a single molecule, by having one or more eTag reporters joined to one or both Xs.

Illustrative compounds include S-(eTag reporter) 3-thiolacrylic acid, N-(eTag reporter), N-methyl 4-amino-4-butenoic acid, O-(eTag reporter), 3-hydroxyacrolein, N-(4-carboxyphenyl) 2-(eTag reporter) imidazole, oxazole, and thiazole.

Also of interest are N-alkyl acridinyl derivatives, substituted at the 9 position with a divalent group of the formula:

wherein:

$X^1$ is a heteroatom selected from the group consisting of O, S, N, and Se, usually one of the first three; and A is a chain of at least 2 carbon atoms and usually not more than 6 carbon atoms substituted with an eTag reporter, where preferably the other valences of A are satisfied by hydrogen, although the chain may be substituted with other groups, such as alkyl, aryl, heterocyclic, etc. groups, A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the eTag reporter.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the eTag reporter. The rings may be coumarin, benzoxazine, tetralin, etc.

A. Fluorescent Compounds

Some of the fluorescent compounds employed in the invention have the following formula:

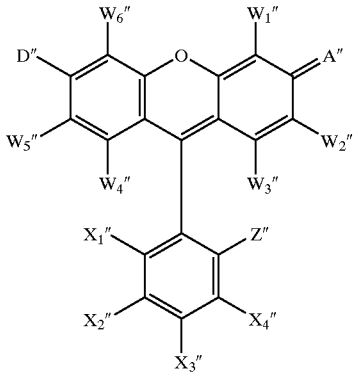

wherein

Z" is COOH, and the like,

A" is O, N($R^{1"}$)($R^{2"}$) wherein $R^{1"}$ and $R^{2"}$ are independently lower alkyl, substituted lower alkyl, and the like, D" is OH, $OR^{3"}$ wherein $R^{3"}$ is lower alkyl, substituted lower alkyl, aryl, substituted aryl, and the like, $W^{1"}$ and $W^{6"}$ are independently H, lower alkyl, substituted lower alkyl, COOH, chloro, fluoro, and the like, $W^{2"}$ and $W^{5"}$ are independently H, lower alkyl, substituted lower alkyl, COOH, chloro, fluoro, and the like, $W^{3"}$ and $W^{4"}$ are independently H, lower alkyl, substituted lower alkyl, COOH, chloro, fluoro, and the like, wherein $W^{2"}$ and $W^{3"}$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^{4"}$ and $W^{5"}$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, $X^{1"}$–$X^{4"}$ are independently H, chloro, fluoro, COOH, bromo, iodo, and the like, with the proviso that, when A" is N($R^{1"}$)($R^{2"}$) and none of $W^{1"}$–$W^{6"}$ is carboxyl, $X^{1"}$ and $X^{4"}$ are not chlorine, and with the proviso that, when A" is O and $W^{2"}$ and $W^{3"}$ are taken together to form a benzo ring and $W^{4"}$ and $W^{5"}$ are not taken together to form a benzo ring, $W^{5"}$ is H, halogen, lower alkyl, or COOH, and with the proviso that, when, A" is O and $X^{1"}$ and $X^{4"}$ are chloro, one of $W^{2"}$ or $W^{5"}$ is not chloro, or when, A" is O and $W^{2"}$ and $W^{5"}$ are chloro, one of $X^{1"}$ or $X^{4"}$ is not chloro, and with the proviso that, when Z is COOH and one of $X^{1"}$–$X^{4"}$ is COOH, one of $W1"$–$W^{6"}$ is other than hydrogen.

Certain embodiments of the invention are compounds of the above formula wherein:

Z" is COOH,

A" is O,

D" is OH, $W^{1"}$ and $W^{6"}$ are independently H or lower alkyl, $W^{2"}$ and $W^{5"}$ are independently H, lower alkyl, COOH, or chloro, $W^{3"}$ and $W^{4"}$ are independently H or lower alkyl, wherein $W^{2"}$ and $W^{3"}$ may be taken together to form a benzo ring, and wherein $W^{4"}$ and $W^{5"}$ may be taken together to form a benzo ring, $X^{1"}$–$X^{4"}$ are independently H, chloro, fluoro, or COOH.

In one embodiment Z" is carboxyl, $W^{6"}$ and $W^{1"}$ are lower alkyl, $W^{5"}$ and $W^{2"}$ are halogen, $X^{2"}$ and $X^{3"}$ are hydrogen or carboxyl and $X^{1"}$ and $X^{4"}$ are hydrogen or halogen. In another embodiment the compounds of the invention are those set forth in FIG. 1 wherein EX is excitation wavelength, EM is wavelength of emission and RQY is quantum yield and the charge for each of the compounds is –3.

Lower alkyl means a straight or branched chain hydrocarbon moiety comprising from 1 to 9 carbon atoms such as, for example, methyl, ethyl, propyl, butyl, pentyl, hexyl, heptyl, octyl, nonyl, and any appropriate iso-, tert-, neo-, sec-, and other forms thereof such as, for example, isobutyl, sec-butyl, tert-butyl, and so forth. Substituted lower alkyl means lower alkyl comprising one or more substituents replacing hydrogen atoms of the hydrocarbon. The substituents may be aliphatic or aromatic and include, for example, alkyl, aryl, aralkyl, halogen (chlorine, fluorine, bromine, iodine), amino, amido, nitro, sulfo, cyano, and so forth.

Figure 2:
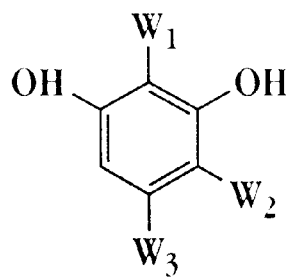
FIG. 2 depicts a general formula for resorcinols that may be used in preparing the compounds employed in the present invention.
Figure 3:
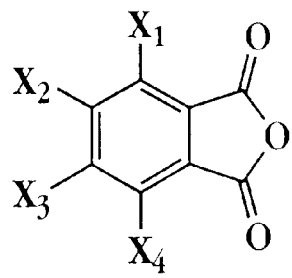
FIG. 3 depicts a general formula for phthalic acid anhydrides that may be used in preparing the compounds employed in the present invention.
Figure 4:
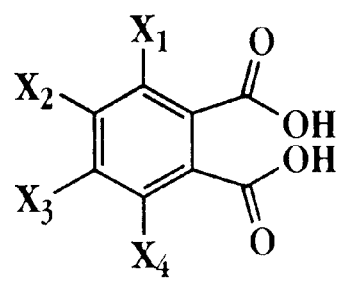
FIG. 4 depicts a general formula for phthalic acids that may be used in preparing the compounds employed in the present invention.
Figure 5:
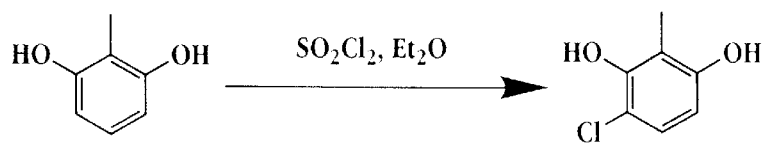
FIG. 5 depicts one approach to the synthesis of 2-methyl-4-chlororesorcinol.
Figure 6:
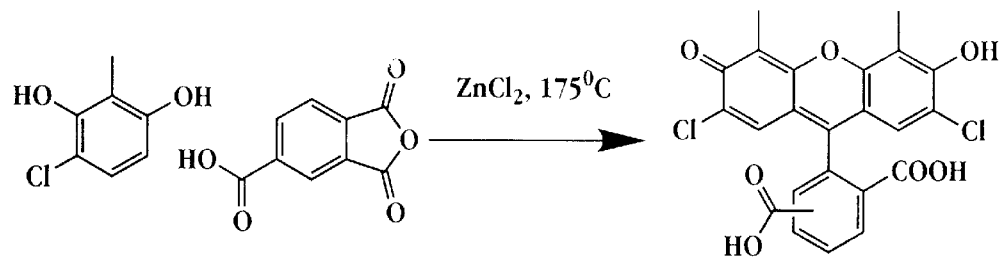
FIG. 6 depicts one approach to the synthesis of AMD-S 001.

The aforementioned fluorescent compounds may be synthesized in a number of different synthetic approaches such as those represented in FIGS. 5–8. These approaches generally involve the reaction of an appropriate resorcinol, as generally represented in FIG. 2, with an appropriate phthalic acid anhydride, as generally represented in FIG. 3, or an appropriate phthalic acid, as generally represented in FIG. 4, with heating in the presence of a suitable condensation catalyst. In the approach of FIG. 6, an example of the condensation reaction is carried out at elevated temperature of about 150 to about 200° C., usually, about 175° C. A condensation catalyst is employed such as, for example, zinc chloride, aluminum chloride, and the like. In the example in the approach of FIG. 8, the appropriate resorcinol and phthalic acid anhydride are heated at an elevated temperature, usually, about 100 to about 150° C., more usually, about 130° C. The catalyst for condensation in this approach may be any acid suitable for condensation reactions of this type such as, for example, methane sulfonic acid, tosic acid, and the like. By choosing the appropriately substituted resorcinol and phthalic acid anhydride, the aforementioned fluorescent compounds may be synthesized. Examples of resorcinols employed to prepare the aforementioned fluorescent compounds are set forth in FIG. 9 ((1) 2,4-dihydroxybenzoic acid; (2) 2,6-dihydroxybenzoic acid; (3) 2-methylresorcinol; (4) 4-chlororesorcinol; (5) 3,5-dihydroxybenzoic acid; (6) 4-ethylresorcinol; (7) 2,4-dimethylresorcinol; (8) 2-methyl-4-chlororesorcinol; (9) 1,3-dihydroxynaphthalene; (10) 2,5-dimethylresorcinol; (11) 2,5-dimethyl-4-chlororesorcinol; (12) 4-hexylresorcinol).

The present methods may be used to synthesize both symmetrical and unsymmetrical fluorescent compounds as well as various regioisomers. The synthesis of unsymmetrical fluorescein derivatives employs a benzophenone intermediate that is a decomposition product of a carboxy fluorescein synthesized from an acid anhydride and the first of two different resorcinols. The benzophenone is subsequently reacted with the second of the two different resorcinols, under conditions that are similar to or identical to those described above for the symmetrical fluorescein derivatives, to generate the desired material. Isolation is also as described for the symmetrical fluorescein derivatives.

The present fluorescent compounds may be employed in any manner in which fluorescent compounds are utilized. One particularly attractive use of the aforementioned fluorescent compounds is as labels in diagnostic procedures. As such, the fluorescent compounds may be associated with a wide variety of entities, for example, to form probes and other fluorescently labeled reagents. The entities may be synthetic or naturally occurring, and may be, for example, nucleotides, nucleosides, polynucleotides, amino acids, poly (amino acids), polysaccharides, haptens, antigens, antibodies and other receptors, supports such as particles including beads and the like, organic and inorganic polymers, cells, microorganisms, and so forth and combinations thereof.

The association of the fluorescent compound with another entity depends on the nature of the other entity and the fluorescent compound. The association may be by attachment, physical absorption, incorporation, electrostatic attraction, hydrogen bonding, and so forth. Methods for attaching fluorescent compounds to other entities are well-known in the art. The attachment may be covalent or non-covalent, direct by virtue of a bond or indirect through the intermediacy of a linking group. The linking group will vary depending upon the nature of the molecules being linked. Functional groups that are normally present or are introduced on a molecule to be linked or on the fluorescent compound may be employed for linking these materials.

In one approach, carbonyl functionalities are used, both oxocarbonyl, e.g., aldehyde, and non-oxocarbonyl (including nitrogen and sulfur analogs) e.g., carboxy, amidine, amidate, thiocarboxy and thionocarboxy. Alternative functionalities include active halogen, diazo, mercapto, olefin, particularly activated olefin, amino, phosphoro and the like. A description of linking groups may be found in U.S. Pat. No. 3,817,837, which disclosure is incorporated herein by reference in its entirety. See also, for example, "Immobilized Enzymes," Ichiro Chibata, Halsted Press, New York (1978) and Cuatrecasas, *J. Biol. Chem.*, 245:3059 (1970).

The linking groups may vary from a bond to a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen. As a general rule, the length of a particular linking group can be selected arbitrarily to provide for convenience of synthesis and the incorporation of any desired group. The linking groups may be aliphatic or aromatic, although with diazo groups, aromatic groups are usually involved.

When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is generally bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, a linking group will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester. These functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are also formed. Where aldehyde and an amine are linked under reducing conditions, an alkylamine is formed. Where a carboxylic acid or phosphate acid and an alcohol are linked, esters are formed.

In one specific embodiment of the present invention the fluorescent compounds are part of an e-tag reporter group as discussed hereinbelow. In this embodiment a fluorescent compound comprises a mobility modifier to form the e-tag reporter group, which is linked to a target-binding moiety by means of a bond or a linking group. In one embodiment the e-tag reporter group is releasable. Usually, this involves linking through a cleavable linkage.

Another aspect of the invention involves phosphoramidite reagents comprising the present fluorescent compounds. The phosphoramidite reagents may be prepared from the fluorescent compounds and may be used in the synthesis of polynucleotides and the like as discussed briefly here and in more detail below. Such reagents are particularly useful for the automated synthesis of labeled polynucleotides comprising one or more fluorescent compounds of the invention. The labeled phosphoramidite reagents may be reacted with a 5'-hydroxyl group of a nucleotide or polynucleotide to form a phosphite ester, which is oxidized to give a phosphate ester. The foregoing chemistry of the synthesis of polynucleotides is described in detail, for example, in Caruthers, *Science* 230: 281–285, 1985; Itakura, et al., *Ann. Rev. Biochem.* 53: 323–356; Hunkapillar, et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, 5,869,643 and elsewhere. The phosphoramidite and phosphite triester approaches are most broadly used, but other approaches include the phosphodiester approach, the phosphotriester approach and the H-phosphonate approach.

The phosphoramidite derivatives of the present fluorescent compounds may be synthesized by methods that are well-known in the art. Briefly, phenolic or other hydroxyls of the fluorescent compounds are protected with suitable protecting groups that can be removed with a deprotection agent employed in the polynucleotide synthesis such as, for example, ammonia, ethanolamine, methylamine/ammonium hydroxide, sodium hydroxide, other sources of hydroxide, and so forth. The protecting groups include by way of illustration and not limitation esters of benzoic acid, esters of pivalic acid, esters of isobutyric acid, 2-nitrobenzyl ether, and the like. A linking moiety of the fluorescent compound such as a carboxyl group is activated with a suitable activating agent such as, for example, carbodiimide, N-hydroxysuccinimide, hydroxy benztriazole, and so forth. The activated linking moiety is reacted with an alcohol linker such as, e.g., an aminoalcohol, diamine addition followed by coupling with an acid alcohol, and the like, to give the protected fluorescent compound with a free alcohol group. The resultant compound with free alcohol functionality is reacted with a phosphitylating agent using standard procedures.

Other fluorescent compounds have the following formula:

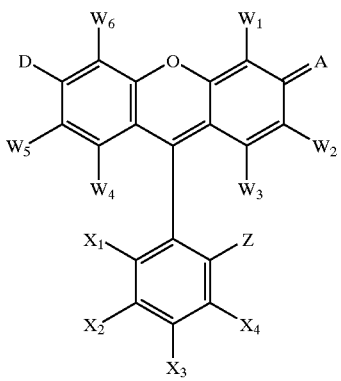

wherein:

Z is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, phosphorus containing species such as, e.g., phosphate, phosphite, and the like, polymer chains of from about 2 to about 10 monomer units such as, e.g. polyethylene glycol, polyamide, polyether, and the like, A is O, $N^+(R^1)(R^2)$ wherein $R^1$ and $R^2$ are independently H, lower alkyl, substituted lower alkyl, and the like, D is OH, $OR^3$ wherein $R^3$ is lower alkyl, substituted lower alkyl, aryl, substituted aryl, and the like, $N(R^1)(R^2)$ wherein $R^1$ and $R^2$ are independently H, lower alkyl, substituted lower alkyl, and the like, $W^1$, $W^2$, $W^3$, $W^4$, $W^5$ and $W^6$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, $X^1$–$X^4$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, wherein $W^2$ and $W^3$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^4$ and $W^5$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, with the proviso that, when A is O, $W^5$ is not phenyl, substituted phenyl, polycyclic aromatic, substituted polycyclic aromatic, heterocyclic, or substituted heterocyclic, and with the proviso that, when A is $N(R^1)(R^2)$ and none of $W^1$–$W^6$ is carboxyl, $X^1$ and $X^4$ are not chlorine, and with the proviso that, when A is O and one of $W^1$ or $W^2$ is lower alkyl or lower alkoxy, one of $W^5$ or $W^6$ is not hydrogen or halogen, and with the proviso that, when A is O, one of $W^2$, $W^5$, $X^1$ or $X^4$ is not chlorine, and with the proviso that, when A is O and one of $W^2$ or $W^5$ is aliphatic hydrocarbylene, one of $W^1$, $W^3$, $W^4$ or $W^6$ is not hydrogen, and with the proviso that, when A is O and one of $W^1$ or $W^6$ is alkoxy or thioalkyl, one of $W^3$ or $W^4$ is not hydrogen, and with the proviso that, when Z is COOH and one of $X^{1''}$–$X^{4''}$ is COOH, one of $W1''$–$W^{6''}$ is other than hydrogen.

Lower alkenyl means a hydrocarbon similar to lower alkyl described above but having at least one carbon-carbon double bond and thus from 2 to 9 carbon atoms. Substituents on a lower alkenyl group may be as described above for substituted lower alkyl.

Lower alkynyl means a hydrocarbon similar to lower alkyl described above but having at least one carbon-carbon triple bond and thus from 2 to 9 carbon atoms. Substituents on a lower alkynyl group may be as described above for substituted lower alkyl.

Other fluorescent compounds include those having the following formula:

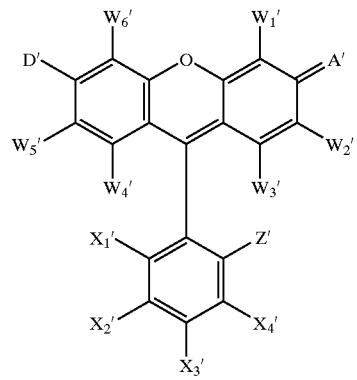

wherein:

Z' is COOH,

A' is O,

D' is OH, $OR^{3'}$ wherein $R^{3'}$ is lower alkyl, substituted lower alkyl, aryl, substituted aryl, $W^{1'}$, $W^{2'}$, $W^{3'}$, $W^{4'}$ and $W^{6'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, $W^{5'}$ is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, chlorine, fluorine, bromine, iodine, COOH, carboxylate, amide, nitrile, nitro, sulfonyl, sulfate, sulfone, amino, tethered amino, quaternary amino, imino, and the like, $X^{1'}$–$X^{4'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, wherein $W^{2'}$ and $W^{3'}$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^{4'}$ and $W^{5'}$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, with the proviso that one of $W^{2'}$, $W^{5'}$, $X^{1'}$ or $X^{4'}$ is not chlorine, and with the proviso that, when one of $W^{1'}$ or $W^{2'}$ is lower alkyl or lower alkoxy, one of $W^{5'}$ or $W^{6'}$ is not hydrogen or halogen, and with the proviso that, when one of $W^{2'}$ or $W^{5'}$ is aliphatic hydrocarbylene, one of $W^{1'}$, $W^{3'}$, $W^{4'}$ or $W^{6'}$ is not hydrogen, and with the proviso that, when one of $W^{1'}$ or $W^{6'}$ is alkoxy or thioalkyl, one of $W^{3'}$ or $W^{4'''}$ is not hydrogen, and with the proviso that, when Z is COOH and one of $X^{1''}$–$X^{4''}$ is COOH, one of $W1'$–$W^{6''}$ is other than hydrogen.

B. Definitions

In defining the terms below, it is useful to consider the makeup of the "electrophoretic probes" that form part of the invention and/or are used in practicing the method of the invention. An electrophoretic probe has four basic components or moieties: (i) a detection group or moiety, (ii) a mobility modifier, (iii) a target-binding moiety, and (iv) a linking group that links the mobility modifier and detection group to the target-bonding moiety. These terms will first be examined in the context of the functioning of the electrophoretic probes in the invention, then more fully defined by their structural features.

The function of an electrophoretic probe in the invention is first to interact with a target, such as a single-stranded nucleic acid, a protein, a ligand-binding agent, such as an antibody or receptor, or an enzyme, e.g., as an enzyme substrate. The "portion", "region" or "moiety" of the probe which binds to the target is the "target-binding moiety" or "target-binding region" or "target-binding portion" ("T"). After the target-binding moiety of an electrophoretic probe binds to a target, and typically as a result of such binding, the linking group of the electrophoretic probe may be cleaved to release an "electrophoretic tag" or "e-tag" or "e-tag reporter" that has a unique mass or charge-to-mass ratio, rendering such e-tags separable by, for example, electroseparation or mass spectrometry. In one embodiment the e-tags have a unique electrophoretic mobility in a defined electrophoretic system. The e-tag reporter is composed of the detection group, mobility modifier, and any residue of the linking group that remains associated with released reporter e-tag after cleavage. Therefore, the second function of the electrophoretic probe is to release an e-tag reporter, which can be identified according to its unique and known electrophoretic mobility.

According to an important feature of the invention, there is provided a set of electrophoretic probes, each of which has a unique target-binding moiety and an associated "e-tag moiety" that imparts to the associated e-tag reporter, a unique electrophoretic mobility by virtue of a unique charge to mass ratio. In general, the unique charge to mass ratio of an e-tag moiety is due to the chemical structure of the mobility modifier, since the detection group and linking-group residue (if any) are generally common to any set of electrophoretic probes. However, it is recognized that the detection group can make unique charge and/or mass contributions to the e-tag reporters as well. For example, a set of electrophoretic probes may be made up of a first subset having a group of mobility modifiers that impart unique electrophoretic mobilities to the subset in combination with a detection group having one defined charge and/or mass, and a second subset having the same group of mobility modifiers in combination with a second detection group with a different charge and/or mass, thus to impart electrophoretic mobilities which are unique among both subsets.

The different target-binding moieties in a set of electrophoretic probes are typically designated "$T_j$", where the set of probes contains n members, and each $T_j$, j=1 to j=n is different, i.e., will bind specifically and/or with unique affinities to different targets. A set of electrophoretic probes of the invention typically includes at least about 5 members, i.e., n is preferably 5 or more, typically 10–100 or more.

A "reporter moiety" "R" or a "detection group" "D" are equivalent terms referring to a chemical group or moiety that is capable of being detected by a suitable detection system, particular in the context of detecting molecules containing the detection group after or during electrophoretic separation. The detection group in accordance with the present invention is a fluorescent compound as disclosed herein. The fluorescent compounds can be readily detected during or after electrophoretic separation of molecules by illuminating the molecules with a light source in the excitation wavelength and detecting fluorescence emission from the irradiated molecules. Exemplary fluorescent compounds will be given below. As noted above, the detection group is typically common among a set or subset of different electrophoretic probes, but may also differ among probe subsets, contributing to the unique electrophoretic mobilities of the released e-tag reporter.

The "mobility modifier" "M" is a generally a chemical group or moiety that is designed to have a particular charge to mass ratio, and thus a particular electrophoretic mobility in a defined electrophoretic system. Exemplary types of mobility modifiers are discussed below. In a set of n electrophoretic probes, each unique mobility modifier is designated $M_j$, where j=1 to n, as above. The mobility modifier may be considered to include a mass-modifying region and/or a charge-modifying region or a single region that acts as both a mass- and charge-modifying region. The mobility modifying region may also be referred to as M*, C*, L, a bond, a linking group, a mobility/mass identifying region or "mir", a charge-imparting moiety and a mobility region.

The detection group and mobility modifier in the electrophoretic probe form an "e-tag moiety," which is linked to the target-binding moiety by a "linking group." The linking group may be only a covalent bond that is cleavable under selected cleaving conditions, or a chemical moiety or chain, such as, for example, a nucleotide and associated phosphodiester bond, an oligonucleotide with an internal cleavable bond, an oligopeptide, or an enzyme substrate, that contains a cleavable chemical bond. Cleavage typically occurs as the result of binding of the probe to the target, which is followed by enzyme or catalyzed cleavage of the linking-group bond or other type of cleavage depending on the nature of the cleavable linkage. The linking group is referred to herein as "L."

The linking group may or may not contribute a linking-group "residue" to the released e-tag reporter, also dependent on the nature of the linking group and the site of cleavage. For example, where the linking group is a covalent bond, or cleavage of the linking group occurs immediately adjacent the "e-tag moiety", the linking group leaves no residue, i.e., will not contribute additional mass and charge to the released e-tag reporter. Similarly, where the linking group is a chemical group or chain that is cleaved internally or immediately adjacent the target-binding moiety, cleavage of the linking group leaves a residual mass and possible charge, contribution to the released e-tag reporter. In general, this contribution will be relatively small, and the same for each different released e-tag (assuming a common linking group within the probe set). As such, generally, the residue will not effect the relative electrophoretic mobilities of the released e-tag reporters, nor the ability to resolve the e-tag reporters into electrophoretic species that can be uniquely identified.

The following definitions are to be understood in the context of the above function of the various components of electrophoretic probes and e-tag reporters. In some case, structure designations based on different lettering schemes are employed, and the equivalency between or among structures with different lettering schemes will be understood by those skilled in the art, in view of the intended function of the structure being referred to.

An "electrophoretic probe" refers to one of a set of probes of the type described above having unique target-binding moieties and associated e-tag moieties. The probes are variously expressed by the following equivalent forms herein:

(a) $(D, M_j)$—L—$T_j$, or $(D, M_j)$—N—$T_j$, where D is a detection moiety, $M_j$ is the jth mobility modifier, Tj is the jth target binding agent, and the linking group is represented by L and by N (when the linking group is the 5'-terminal nucleotide of an oligonucleotide target-binding moiety). In this and the following structural designations, $(D, M_j)$— indicates that either the detection group or the mobility modifier is joined to the linking group, i.e., either $(D, M_j)$ or $(M_j, D)$—.

(b) $(R, M_j)$—L—$T_j$, or $(R, M_j)$—N—$T_j$, where R is a detection moiety or reporter group, and $M_j$, Tj, and L and N are as in (a).

(c) R—L—T or L—R—T, where R is a label, particularly a fluorescer, L is a mir, a bond or a linking group, where L and the regions to which L is attached provide for the variation in mobility of the e-tags. T comprises a portion of the target-binding region, particularly a nucleoside base, purine or pyrimidine, and is the base, a nucleoside, nucleotide or nucleotide triphosphate, an amino acid, either naturally occurring or synthetic, or other functionality that may serve to participate in the synthesis of an oligomer, when T is retained, and is otherwise a functionality resulting from the cleavage between L, the mir, and the target-binding region. (in the corresponding e-tag reporter).

A "set" or "group", "plurality" or "library" of electrophoretic probes refers to a plurality of electrophoretic probes having typically at least five, typically 10–100 or more probes with different unique target-binding moieties and associated e-tag moieties.

As used herein, the term "electrophoretic tag probe set" or "e-tag probe set" refers to a set of probes for use in detecting each or any of a plurality of known, selected target nucleotide sequences, or for detecting the binding of, or interaction between, each or any of a plurality of ligands and one or more target antiligands.

The term "target-binding moiety" or "$T_j$" refers to the component of an e-tag probe that participates in recognition and specific binding to a designated target. The target-binding moiety may also be referred to as T or T', or may be defined based on the type of target, e.g., as a snp detection sequence or an oligonucleotide detection sequence.

In one application of this embodiment, the e-tag probe is referred to as a snp detection sequence, a fluorescence snp detection sequence or an oligonucleotide detection sequence.

In another generalized embodiment for use in detection of non-nucleic acid targets, the target-binding moiety, $T_j$, is or includes a ligand capable of binding to or interacting with a target antiligand and L is a linking group connected to $T_j$ by a bond that is cleavable by a selected cleaving agent when the probe is bound to or interacting with the target antiligand. L may also be referred to as "L", a terminal linking region, a terminal linking group.

"Electrophoretic tag" refers to a composition or reagent for unique identification of an entity of interest during separation. An e-tag has the fundamental structure given as $(D, M_j)$—L, where D and $M_j$ are the detection group and jth mobility modifier, as defined above, and L is the linking group, and in particular, the bond or residue of the linking group remaining after cleavage. Here the e-tag moiety $(D, M_j)$ is intended to include both of the structures D—$M_j$—L and $M_j$—D—L. Other equivalent forms of expressing the e-tag are: $(R, M_j)$, $(R, M)$, R—L or L—R where R is a reporter group, $M_j$ or M is a mobility modifier and L is a mobility identifying region (mir), a bond or a linking group.

For purposes of clarity, the concept of an electrophoretic tag is consistently referred to herein as an "e-tag", however various references to "Etag", "ETAG", "eTAG" and "eTag" may be made when referring to an electrophoretic tag. As used herein, the term "electrophoretic tag probe" or "e-tag probe" refers to a reagent used for target recognition, which comprises an e-tag and a target-binding moiety. Upon interaction with the corresponding target, the e-tag undergoes a change resulting in the release of an e-tag reporter. Such an e-tag probe may also be referred to as a binding member.

E-tag probes of the invention find utility in performing multiplexed for detection/analysis of targets including, but not limited to nucleic acid detection, such as sequence recognition, snp detection, transcription analysis or mRNA determination, allelic determination, mutation determination, HLA typing or MHC determination and haplotype determination, in addition to detection of other ligands, such as proteins, polysaccharides, etc.

As used herein, the term "e-tag reporter" refers to the cleavage product generated as a result of the interaction between an e-tag probe and its target. In one representation, an e-tag reporter comprises the e-tag plus a residual portion of the target binding moiety ($T_j$) (where, as in the nucleotide example, above, one or more nucleotides in the target-binding moiety contain the cleavable linking group), or a residual portion of the linking group (when the latter is considered separate from the target-binding moiety). In another embodiment, the e-tag does not retain any of the target-binding moiety. E-tag reporters can be differentiated by electrophoretic mobility or mass and are amenable to electrophoretic separation and detection, although other methods of differentiating the tags may also find use.

An e-tag reporter resulting from the interaction of an e-tag probe and a nucleic acid target typically has the form (D, $M_j$)—N, where N is as defined above, the 5'-end terminal nucleotide of a target-binding oligonucleotide.

An e-tag reporter resulting from the interaction of an e-tag probe used to detect the binding of or interaction between a ligand and an antiligand typically has the form (D, $M_j$)—L'. D and $M_j$ are defined above and L' is the residue of L that remains attached to (D, $M_j$) after an e-tag reporter is cleaved from the corresponding e-tag probe.

E-tag reporters may also be described as electrophoretic tags or eTags for use in electrophoresis, released eTags, released e-tags, etc. The e-tag for use in electrophoresis may also be represented by the formula: R—L—T, as described above, where T is retained, and is otherwise a functionality resulting from the cleavage between L, the mir, and the target-binding region.

As used herein, the term "binding event" generally refers to the binding of the target-binding moiety of an e-tag probe to its target. By way of example, such binding may involve the interaction between complementary nucleotide sequences or the binding between a ligand and target antiligand.

As used herein, the term "capture ligand", refers to a group that is typically included within the target binding moiety or portion of an e-tag probe and is capable of binding specifically to a "capture agent" or receptor. The interaction between such a capture ligand and the corresponding capture agent may be used to separate uncleaved e-tag probes from released e-tag reporters.

C. Electrophoretic Probes

An e-tag may be joined to any convenient site on the target-binding reagent, without interfering with the synthesis, release and/or binding of the e-tag labeled reagent. For nucleotides, the e-tag may be bound to a site on the base, either an annular carbon atom or a hydroxyl or amino substituent. For proteins, the e-tag may be bound to multiple sites either on the protein or through the intermediacy of a hub nucleus.

In mass spectrometry, the e-tags may be different from the e-tags used in electrophoresis, since the e-tags do not require a label or a charge. Thus, these e-tags may be differentiated solely by mass, which can be a result of atoms of different elements, isotopes of such elements, and numbers of such atoms.

Electrophoretic tags are small molecules (molecular weight of 150 to 10,000), which can be used in any measurement technique that permits identification by mass, e.g. mass spectrometry, and or mass/charge ratio, as in mobility in electrophoresis. Simple variations in mass and/or mobility of the electrophoretic tag leads to generation of a library of electrophoretic tags, that can then be used to detect multiple target molecules such as multiple snp's or multiple target sequences or multiple proteins. The electrophoretic tags are easily and rapidly separated in free solution without the need for a polymeric separation media. Quantitation is achieved using internal controls. Enhanced separation of the electrophoretic tags in electrophoresis is achieved by modifying the tags with positively charged moieties.

The e-tags have a mobility modifier that, with the other regions to which the mobility modifier is attached during separation, provide for unique identification of an entity of interest. The mobility modifier of the e-tags can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mir will have from 0 to 40, more usually from 0 to 30 heteroatoms, which in addition to the heteroatoms indicated above will include halogen or other heteroatom. The total number of atoms other than hydrogen will generally be fewer than 200 atoms, usually fewer than 100 atoms. Where acid groups are present, depending upon the pH of the medium in which the mir is present, various cations may be associated with the acid group. The acids may be organic or inorganic, including carboxyl, thionocarboxyl, thiocarboxyl, hydroxamic, phosphate, phosphite, phosphonate, sulfonate, sulfinate, boronic, nitric, nitrous, etc. For positive charges, substituents will include amino (includes ammonium), phosphonium, sulfonium, oxonium, etc., where substituents will generally be aliphatic of from about 1–6 carbon atoms, the total number of carbon atoms per heteroatom, usually be less than about 12, usually less than about 9. The mobility modifier may be neutral or charged depending on the other regions to which the mobility modifier is attached, at least one of the regions having at least one charge. Neutral mirs will generally be polymethylene, halo- or polyhaloalkylene or aralkylene (a combination of aromatic—includes heterocyclic—and aliphatic groups), where halogen will generally be fluorine, chlorine, bromine or iodine, polyethers, particularly, polyoxyalkylene, wherein alkyl is of from 2–3 carbon atoms, polyesters, e.g. polyglycolide and polylactide, dendrimers, comprising ethers or thioethers, oligomers of addition and condensation monomers, e.g. acrylates, diacids and diols, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the e-tag. The mir may be a homooligomer or a heterooligomer, having different monomers of the same or different chemical characteristics, e.g., nucleotides and amino acids. Desirably neutral mass differentiating groups will be combined with short charged sequences to provide the mobility modifier.

The charged mobility modifiers generally have only negative or positive charges, although, one may have a combination of charges, particularly where a region to which the mobility modifier is attached is charged and the mobility modifier has the opposite charge. The mobility modifiers may have a single monomer that provides the different functionalities for oligomerization and carry a charge or two monomers may be employed, generally two monomers. One may use substituted diols, where the substituents are charged and dibasic acids. Illustrative of such oligomers is the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as dibasic acids, such as oxalic acid, malonic acid, succinic acid, maleic acid, fumaric acid, carbonic acid, etc. Instead of using esters, one may use amides, where amino acids or diamines and diacids may be employed. Alternatively, one may link the hydroxyls or amines with alkylene or arylene groups.

By employing monomers that have substituents that provide for charges or which may be modified to provide charges, mobility modifiers may be obtained having the desired mass/charge ratio. For example, by using serine or threonine, the hydroxyl groups may be modified with phosphate to provide negatively charged mobility modifiers. With arginine, lysine and histidine, positively charged mobility modifiers may be obtained. Oligomerization may be performed in conventional ways to provide the appropriately sized mobility modifier. The different mobility modifiers having different orders of oligomers, generally having from 1 to 20 monomeric units, more usually about 1 to 12, where a unit intends a repetitive unit that may have from 1 to 2 different monomers. For the most part, oligomers are used with other than nucleic acid target-binding regions. The polyfunctionality of the monomeric units provides for functionalities at the termini that may be used for conjugation to other moieties, so that one may use the available functionality for reaction to provide a different functionality. For example, a carboxyl group may be reacted with an aminoethylthiol, to replace the carboxyl group with a thiol functionality for reaction with an activated olefin.

Where the e-tags are used for mass detection, as with mass spectrometry, the e-tags need not be charged but merely differ in mass, since a charge will be imparted to the e-tag reporter by the mass spectrometer. Thus, one could use the same or similar monomers, where the functionalities would be neutral or made neutral, such as esters and amides of carboxylic acids. Also, one may vary the e-tags by isotopic substitution, such as $^2$H, $^{18}$O, $^{14}$C, etc.

The e-tag may be linked by a stable bond or one that may be cleavable thermally, photolytically or chemically. There is an interest in cleaving the e-tag from the target-binding moiety in situations where cleavage of the target-binding moiety results in significant cleavage at other than the desired site of cleavage, resulting in satellite cleavage products, such as di- and higher oligonucleotides and this family of products interferes with the separation and detection of the e-tags. However, rather than requiring an additional step in the identification of the tags by releasing them from the base to which they are attached, the target binding sequence can be modified to minimize obtaining cleavage at other than the desired bond, for example, the ultimate or penultimate phosphate link in a nucleic acid sequence. For immunoassays involving specific binding members, bonding of the e-tag will usually be through a cleavable bond to a convenient functionality, such as carboxy, hydroxy, amino or thiol, particularly as associated with proteins, lipids and saccharides.

If present, the nature of the releasable or cleavable link may be varied widely. Numerous linkages are available, which are thermally, photolytically or chemically labile. See, for example, U.S. Pat. No. 5,721,099. Where detachment of the product from all or a portion of the target-binding region is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may serve. By combining formaldehyde, HCl and an alcohol moiety, an α-chloroether is formed. This may then be coupled with a hydroxy functionality to form the acetal. Various photolabile linkages may be employed, such as o-nitrobenzyl, 7-nitroindanyl, 2-nitrobenzhydryl ethers or esters, etc.

For a list of cleavable linkages, see, for example, Greene and Wuts, Protective Groups in Organic Synthesis, $2^{nd}$ ed. Wiley, 1991. The versatility of the various systems that have been developed allows for broad variation in the conditions for attachment of the e-tag entities.

Various functionalities for cleavage are illustrated by: silyl groups being cleaved with fluoride, oxidation, acid, bromine or chlorine; o-nitrobenzyl with light; catechols with cerium salts; olefins with ozone, permanganate or osmium tetroxide; sulfides with singlet oxygen or enzyme catalyzed oxidative cleavage with hydrogen peroxide, where the resulting sulfone can undergo elimination; furans with oxygen or bromine in methanol; tertiary alcohols with acid; ketals and acetals with acid; α- and β-substituted ethers and esters with base, where the substituent is an electron withdrawing group, e.g., sulfone, sulfoxide, ketone, etc., and the like.

The linker or mobility modifier may be joined in any convenient manner to a unit of the target-binding region, such as the base of the nucleoside or the amino acid of a protein. Various functionalities that may be used include alkylamine, amidine, thioamide, ether, urea, thiourea, guanidine, azo, thioether and carboxylate, sulfonate, and phosphate esters, amides and thioesters.

The linkers may be oligomers, where the monomers may differ as to mass and charge. For convenience and economy, monomers will generally be commercially available, but if desired, they may be originally synthesized. Monomers which are commercially available and readily lend themselves to oligomerization include amino acids, both natural and synthetic, nucleotides, both natural and synthetic, and monosaccharides, both natural and synthetic, while other monomers include hydroxyacids, where the acids may be organic or inorganic, e.g. carboxylic, phosphoric, boric, sulfonic, etc., and amino acids, where the acid is inorganic, and the like. In some instances, nucleotides, natural or synthetic, may find use. The monomers may be neutral, negatively charged or positively charged. Normally, the charges of the monomers in the linkers will be the same, so that in referring to the mass/charge ratio, it will be related to the same charge. Where the label has a different charge from the linker or mir, this will be treated as if the number of charges is reduced by the number of charges on the linker or mir. For natural amino acids, the positive charges may be obtained from lysine, arginine and histidine, while the negative charges may be obtained from aspartic and glutamic acid. For nucleotides, the charges will be obtained from the phosphate and any substituents that may be present or introduced onto the base. For sugars sialic acid, uronic acids of the various sugars, or substituted sugars may be employed.

The linker L may include charged groups, uncharged polar groups or be non-polar. The groups may be alkylene and substituted alkylenes, oxyalkylene and polyoxyalkylene, particularly alkylene of from 2 to 3 carbon atoms, arylenes and substituted arylenes, polyamides, polyethers, polyalkylene amines, etc. Substituents may include heteroatoms, such as halo, phosphorous, nitrogen, oxygen, sulfur, etc., where the substituent may be halo, nitro, cyano, non-oxo-carbonyl, e.g. ester, acid and amide, oxocarbonyl, e.g. aldehyde and keto, amidine, urea, urethane, guanidine, carbamyl, amino and substituted amino, particularly alkyl substituted amino, azo, oxy, e.g. hydroxyl and ether, etc., where the substituents will generally be of from about 0 to 10 carbon atoms, while L will generally be of from about 1 to 100 carbon atoms, more usually of from about 1 to 60 carbon atoms and preferably about 1 to 36 carbon atoms. L will be joined to the label and the target-binding region by any convenient functionality, such as carboxy, amino, oxy, phospho, thio, iminoether, etc., where in many cases the label and the target-binding region will have a convenient functionality for linkage.

The number of heteroatoms in L is sufficient to impart the desired charge to the label conjugate, usually from about 1 to about 200, more usually from about 2 to 100, heteroatoms. The heteroatoms in L may be substituted with atoms other than hydrogen.

The charge-imparting moieties of L may be, for example, amino acids, tetraalkylammonium, phosphonium, phosphate diesters, carboxylic acids, thioacids, sulfonic acids, sulfate groups, phosphate monoesters, and the like and combinations of one or more of the above. The number of the above components of L is such as to achieve the desired number of different charge-imparting moieties.

In one embodiment, an e-tag for use in electrophoresis may be represented by the formula:

D—L—T wherein D is a fluorescent label, particularly a fluorescent compound disclosed hereinabove, L is a mobility modifier, a bond or a linking group where L and the regions to which L is attached provide for the variation in mobility of the e-tags.

Accordingly, in one embodiment the fluorescent label is a compound of the formula:

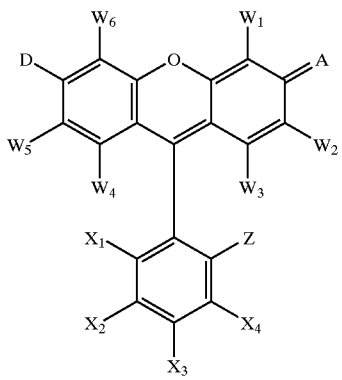

wherein:
Z is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, phosphorus containing species such as, e.g., phosphate, phosphite, and the like, polymer chains of from about 2 to about 10 monomer units such as, e.g. polyethylene glycol, polyamide, polyether, and the like, A is O, $N^+(R^1)(R^2)$ wherein $R^1$ and $R^2$ are independently H, lower alkyl, substituted lower alky, and the like, D is OH, $OR^3$ wherein $R^3$ is lower alkyl, substituted lower alkyl, aryl, substituted aryl, and the like, $N(R^1)(R^2)$ wherein $R^1$ and $R^2$ are independently H, lower alkyl, substituted lower alkyl, and the like, $W^1$, $W^2$, $W^3$, $W^4$, $W^5$ and $W^6$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, $X^1$–$X^4$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, wherein $W^2$ and $W^3$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^4$ and $W^5$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like.

Lower alkenyl and lower alkynyl are defined above.

In one specific embodiment of the aforementioned e-tag moiety set, the fluorescent label is a compound of the formula:

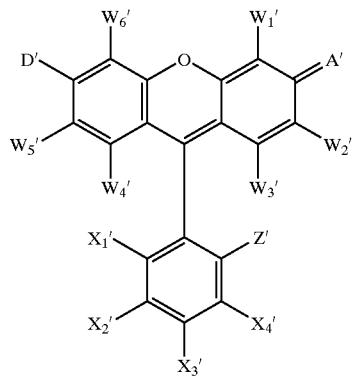

wherein:
Z' is COOH,
A' is O,
D' is OH, $OR^{3'}$ wherein $R^{3'}$ is lower alkyl, substituted lower alkyl, aryl, substituted aryl,
$W^{1'}$, $W^{2'}$, $W^{3'}$, $W^{4'}$ and $W^{6'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, $W^{5'}$ is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, chlorine, fluorine, bromine, iodine, COOH, carboxylate, amide, nitrile, nitro, sulfonyl, sulfate, sulfone, amino, tethered amino, quaternary amino, imino, and the like, $X^{1'}-X^{4'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, wherein $W^{2'}$ and $W^{3'}$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^{4'}$ and $W^{5'}$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like.

In another specific embodiment of the above e-tag moiety, detectable label is a compound of the formula:

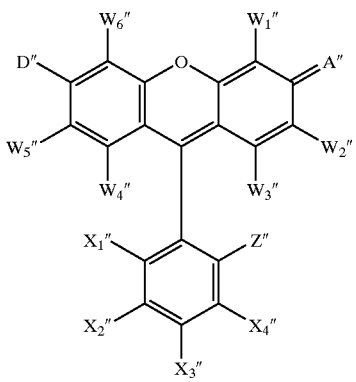

wherein $Z''$ is COOH, and the like, $A''$ is O, $N(R^{1''})(R^{2''})$ wherein $R^{1''}$ and $R^{2''}$ are independently lower alkyl, substituted lower alkyl, and the like, $D''$ is OH, $OR^{3''}$ wherein $R^{3''}$ is lower alky, substituted lower alkyl, aryl, substituted aryl, and the like, $W^{1''}$ and $W^{6''}$ are independently H, lower alkyl, substituted lower alkyl, COOH, chloro, fluoro, and the like, $W^{2''}$ and $W^{5''}$ are independently H, lower alkyl, substituted lower alkyl, COOH, chloro, fluoro, and the like, $W^{3''}$ and $W^{4''}$ are independently H, lower alkyl, substituted lower alkyl, COOH, chloro, fluoro, and the like, wherein $W^{2''}$ and $W^{3''}$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^{4''}$ and $W^{5''}$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, $X^{1''}-X^{4''}$ are independently H, chloro, fluoro, COOH, bromo, iodo, and the like.

In one embodiment $Z''$ is carboxyl, $W^{6''}$ and $W^{1''}$ are lower alkyl, $W^{5''}$ and $W^{2''}$ are halogen, $X^{2''}$ and $X^{3''}$ are hydrogen or carboxyl and $X^{1''}$ and $X^{4''}$ are hydrogen or halogen. In another embodiment the compounds of the invention are those set forth in FIG. 1 wherein EX is excitation wavelength, EM is wavelength of emission and RQY is quantum yield.

Lower alkyl means a straight or branched chain hydrocarbon moiety comprising from 1 to 9 carbon atoms such as, for example, methyl, ethyl, propyl, butyl, pentyl, hexyl, heptyl, octyl, nonyl, and any appropriate iso-, tert-, neo-, sec-, and other forms thereof such as, for example, isobutyl, sec-butyl, tert-butyl, and so forth. Substituted lower alkyl means lower alkyl comprising one or more substituents replacing hydrogen atoms of the hydrocarbon. The substituents may be aliphatic or aromatic and include, for example, alkyl, aryl, aralkyl, halogen (chlorine, fluorine, bromine, iodine), amino, amido, nitro, sulfo, cyano, and so forth.

In another specific embodiment of the above e-tag moiety, the detectable label is a compound wherein $Z''$ is carboxyl, $W^{6''}$ and $W^{1''}$ are lower alkyl, $W^{5''}$ and $W^{2''}$ are halogen, $X^{2''}$ and $X^{3''}$ are hydrogen or carboxyl and $X^{1''}$ and $X^{4''}$ are hydrogen or halogen.

In another specific embodiment of the above e-tag moiety, the detectable label is a compound wherein $Z''$ is carboxyl, $W^{6''}$ and $W^{1''}$ are methyl, $W^{5''}$ and $W^{2''}$ are chloro, one of $X^{2''}$ and $X^{3''}$ are hydrogen and the other is carboxyl and $X^{1''}$ and $X^{4''}$ are hydrogen.

In another specific embodiment of the above e-tag moiety, the detectable label is a compound wherein $Z''$ is carboxyl, $W^{6''}$ and $W^{1''}$ are methyl, $W^{5''}$ and $W^{2''}$ are chloro, one of $X^{2''}$ and $X^{3''}$ are hydrogen and the other is carboxyl and $X^{1''}$ and $X^{4''}$ are chloro.

In another specific embodiment of the above e-tag moiety, the detectable label is a compound selected from the group of compounds of FIG. 1.

T comprises a portion of the target-binding moiety. L provides a major factor in the differences in mobility between the different e-tags, in combination with the label and any residual entity, which remain with the mobility modifier. L may or may not include a cleavable linker, depending upon whether the terminal entity to which L is attached is to be retained or completely removed.

Conjugates of particular interest comprise a fluorescent compound and a different amino acid or combinations thereof in the form of a peptide or combinations of amino acids and thioacids or other carboxylic acids. Such compounds are represented by the formula:

wherein D' is a fluorescent as described above, L' is an amino acid or a peptide or combinations of amino acids and thioacids or other carboxylic acids and T' is a functionality for linking to a nucleoside base or is a nucleoside, nucleotide or nucleotide triphosphate.

In a particular embodiment the label conjugates may be represented by the formula:

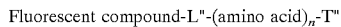

wherein L" is a bond or a linking group of from 1 to 20 atoms other than hydrogen, n is 1 to 20, and T" comprises a nucleoside base, purine or pyrimidine, including a base, a nucleoside, a nucleotide or nucleotide triphosphates, an amino acid, or functionality for linking to the target-binding region. An example of label conjugates in this embodiment, by way of illustration and not limitation, is one in which the fluorescer is a fluorescent compound as described above, L" is a bond in the form of an amide linkage involving the meta-carboxyl of the fluorescein and the terminal amine group of lysine, and T" is a nucleotide triphosphate. These label conjugates may be represented as follows:

Fluorescent compound-(CO)NH—CH(CH$_2$)$_3$CH(NH$_2$) (amino acid)$_n$COX" wherein X is as set forth in Table 1.

TABLE 1

| No. | X |
| --- | --- |
| 1 | OH |
| 2 | NH-lysine |
| 3 | NH-(lysine)$_2$ |
| 4 | NH-alanine |
| 5 | NH-aspartic acid |
| 6 | NH-(aspartic acid)$_2$ |
| 7 | NH-(aspartic acid)$_3$ |
| 8 | NH-(aspartic acid)$_4$ |
| 9 | NH-(aspartic acid)$_5$ |
| 10 | NH-(aspartic acid)$_6$ |
| 11 | NH-(aspartic acid)$_7$ |
| 12 | NH-alanine-lysine |
| 13 | NH-aspartic acid-lysine |
| 14 | NH-(aspartic acid)$_2$-lysine |
| 15 | NH-(aspartic acid)$_3$-lysine |
| 16 | NH-(aspartic acid)$_4$-lysine |
| 17 | NH-(aspartic acid)$_5$-lysine |
| 18 | NH-(aspartic acid)$_6$-lysine |
| 19 | NH-(aspartic acid)$_7$-lysine |
| 20 | NH-(aspartic acid)$_8$-lysine |
| 21 | NH-(lysine)$_4$ |
| 22 | NH-(lysine)$_5$ |

Substituted aryl groups can serve as both mass- and charge-modifying regions. Various functionalities may be substituted onto the aromatic group, e.g. phenyl, to provide mass as well as charges to the e-tag reporter. The aryl group may be a terminal group, where only one linking functionality is required, so that a free hydroxyl group may be acylated, may be attached as a side chain to an hydroxyl present on the e-tag reporter chain, or may have two functionalities, e.g. phenolic hydroxyls, that may serve for phophite ester formation and other substituents, such as halo, haloalkyl, nitro, cyano, alkoxycarbonyl, alkylthio, etc. where the groups may be charged or uncharged.

The fluorescent compound conjugates may be prepared utilizing conjugating techniques that are well known in the art. The charge-imparting moiety L may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to label or to another molecule of the charge-imparting moiety.

Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g. sulfonate, phosphate esters, sulfonamides, thioesters, etc., and the like.

The electrophoretic tags comprise a linker, which provides the linkage between the base and the fluorescent molecule or a functionality that may be used for linking to a fluorescent molecule. By having different functionalities that may be individually bonded to a detectable label, one enhances the opportunity for diversity of the e-tags. Using different fluorescers for joining to the different functionalities, the different fluorescers can provide differences in light emission and mass/charge ratios for the e-tags.

Generally, the electrophoretic tag will have a charge/mass ratio in the range of about –0.0001 to 0.1, usually in the range of about –0.001 to about 0.5. Mobility is $q/M^{2/3}$, where q is the charge on the molecule and M is the mass of the molecule. Desirably, the difference in mobility, under the conditions of an electrophoretic determination, between the closest electrophoretic labels will be at least about 0.001, usually 0.002, more usually at least about 0.01, and may be 0.02 or more.

D. Capture Ligands

Other reagents that are useful include a ligand-modified nucleotide and its receptor. Ligands and receptors include biotin and streptavidin, ligand and antiligand, e.g., digoxin or derivative thereof and antidigoxin, etc. By having a ligand conjugated to the oligonucleotide, one can sequester the e-tag conjugated oligonucleotide probe and its target with the receptor, remove unhybridized e-ag reporter conjugated oligonucleotide and then release the bound e-tag reporters or bind an oppositely charged receptor, so that the ligand-receptor complex with the e-tag reporter migrates in the opposite direction.

E. E-tag Reagents—Synthesis

The chemistry for performing the types of syntheses to form the charge-imparting moiety or mobility modifier as a peptide chain is well known in the art. See, for example, Marglin, et al., *Ann. Rev. Biochem.* (1970) 39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, *J. Am. Chem. Soc.* (1980) 85:2149–2154 and Houghten et al., *Int. J. Pep. Prot. Res.* (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p 46, Academic Press (New York), for solid phase peptide synthesis; and E. Schroder, et al., "The Peptides, vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

In one exemplary approach, after the synthesis of the peptide is complete, the peptide is removed from the resin by conventional means such as ammonolysis, acidolysis and the like. The fully deprotected peptide may then be purified by techniques known in the art such as chromatography, for example, adsorption chromatography, ion exchange chromatography, partition chromatography, high performance liquid chromatography, thin layer chromatography, and so forth.

As can be seen, the selected peptide representing a charge-imparting moiety may be synthesized separately and then attached to the label either directly or by means of a linking group. On the other hand, the peptide may be synthesized as a growing chain on the label. In any of the above approaches, the linking of the peptide or amino acid to the label may be carried out using one or more of the techniques described above for the synthesis of peptides or for linking moieties to labels.

Synthesis of e-tags comprising nucleotides can be easily and effectively achieved via assembly on a solid phase support during probe synthesis, using standard phosphoramidite chemistries. The e-tags are assembled at the 5'-end of probes after coupling of a final nucleosidic residue, which becomes part of the e-tag during the assay. In one approach, the e-tag probe is constructed sequentially from a single or several monomeric phosphoramidite building blocks (one containing a dye residue), which are chosen to generate tags with unique electrophoretic mobilities based on their mass to charge ratio. The e-tag probe is thus composed of monomeric units of variable charge to mass ratios bridged by phosphate linkers. The penultimate coupling during probe synthesis is initially carried out using commercially available modified (and unmodified) phosphoramidites.

The e-tag may be assembled having an appropriate functionality at one end for linking to the binding compound. For oligonucleotides, a phosphoramidite or phosphate ester at the linking site may be used to bond to an oligonucleotide chain, either 5' or 3', particularly after the oligonucleotide has been synthesized, while still on a solid support and before the blocking groups have been removed. While other techniques exist for linking the oligonucleotide to the e-tag, such as having a functionality at the oligonucleotide terminus that specifically reacts with a functionality on the e-tag, such as maleimide and thiol, or amino and carboxy, or amino and keto under reductive amination conditions, the phosphoramidite addition is preferred. For a peptide-binding compound, a variety of functionalities can be employed, much as with the oligonucleotide functionality, although phosphoramidite chemistry may only occasionally be appropriate. Thus, the functionalities normally present in a peptide, such as carboxy, amino, hydroxy and thiol may be the targets of a reactive functionality for forming a covalent bond.

F. Sets of E-tags

The libraries will ordinarily have at least about 5 members, usually at least about 10 members, and may have 100 members or more, for convenience generally having about 50–75 members. Some members may be combined in a single container or be provided in individual containers, depending upon the region to which the mobility modifier is attached. The members of the library will be selected to provide clean separations in electrophoresis, when capillary electrophoresis is the analytical method. To that extent, mobilities will differ as described above, where the separations may be greater, the larger the larger the number of molecules in the band to be analyzed. Particularly, non-sieving media may be employed in the separation.

Besides the nature of the linker or mobility modifier, as already indicated, diversity can be achieved by the chemical and optical characteristics of the fluorescent compound, the use of energy transfer complexes, variation in the chemical nature of the linker, which affects mobility, such as folding, interaction with the solvent and ions in the solvent, and the like. As already suggested, the linker will usually be an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, a side chain functionality may be distinguished from a terminal amino acid functionality. Also, by appropriate design, preferential reaction may be provided between the same functionalities present at different sites on the linking group. The choice between synthesis and cloning for preparation of oligopeptides will to a substantial degree depend on the length of the linker.

Depending upon the reagent to which the e-tag is attached, there may be a single e-tag or a plurality of e-tags, generally ranging from about 1–100, more usually ranging from about 1–40, more particularly ranging from about 1–20. The number of e-tags bonded to a single target-binding moiety will depend upon the sensitivity required, the solubility of the e-tag conjugate, the effect on the assay of a plurality of e-tags, and the like. For oligomers or polymers, such as nucleic acids and poly(amino acids), e.g. peptides and proteins, one may have one or a plurality of e-tags, while for synthetic or naturally occurring non-oligomeric compounds, usually there will be only 1–3, more usually 1–2 e-tags.

For 20 different e-tag reporters, only 5 different mobility modifiers are required, one phosphate link and four different detectable regions. For 120 e-tag reporters, only 10 different mobility modifiers are needed, 3 different charge-modifying regions and 4 different detectable regions. For 500 different e-tag reporters, only 25 different mobility modifiers are necessary, 5 different charge-modifying regions and 4 different detectable regions.

As mentioned above, one embodiment of the present invention is a set of electrophoretic tag (e-tag) probes for detecting the binding of or interaction between each or any of a plurality of ligands and one or more target antiligands. The set comprises j members, and each of said e-tag probes having the form:

(D, M$_j$)—L—T$_j$, where
(a) D is a detection group comprising a detectable label;
(b) T$_j$ is a ligand capable of binding to or interacting with a target antiligand,
(c) L is a linking group connected to T$_j$ by a bond that is cleavable by a selected cleaving agent when the probe is bound to or interacting with the target antiligand, wherein cleavage by said agent produces an e-tag reporter of the form (D, M$_j$)—L', where L' is the residue of L attached to (D, M$_j$) after such cleavage,
(d) M$_j$ is a mobility modifier that imparts a unique and known electrophoretic mobility to a corresponding e-tag reporter of the form (D, M$_j$)—L', within a selected range of electrophoretic mobilities with respect to other e-tag reporters of the same form in the probe set; and
(e) (D, M$_j$)— includes both D—M$_j$— and M$_j$—D—;
wherein the detectable label is a compound of the formula:

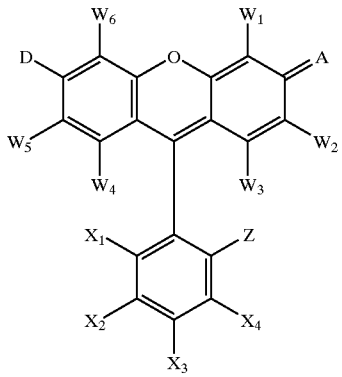

wherein:
Z is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, phosphorus containing species such as, e.g., phosphate, phosphite, and the like, polymer chains of from about 2 to about 10 monomer units such as, e.g. polyethylene glycol, polyamide, polyether, and the like, A is O, N$^+$(R$^1$)(R$^2$) wherein R$^1$ and R$^2$ are independently H, lower alkyl, substituted lower alkyl, and the like, D is OH, OR$^3$ wherein R$^3$ is lower alkyl, substituted lower alky, aryl, substituted aryl, and the like, N(R$^1$)(R$^2$) wherein R$^1$ and R$^2$ are independently H, lower alkyl, substituted lower alkyl, and the like, W$^1$, W$^2$, W$^3$, W$^4$, W$^5$ and W$^6$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, X$^1$–X$^4$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, wherein W$^2$ and W$^3$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein W$^4$ and W$^5$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, Lower alkenyl and lower alkynyl are defined above.

In one specific embodiment of the aforementioned probe set, the detectable label is a compound of the formula:

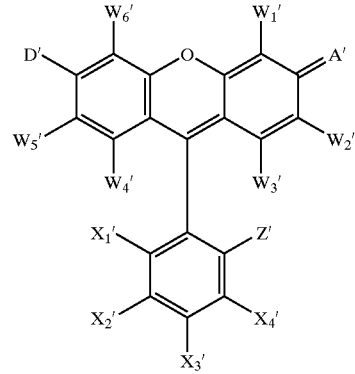

wherein:
Z' is COOH,
A' is O,
D' is OH, OR$^{3'}$ wherein R$^{3'}$ is lower alkyl, substituted lower alkyl, aryl, substituted aryl,
W$^{1'}$, W$^{2'}$, W$^{3'}$, W$^{4'}$ and W$^{6'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, $W^{5'}$ is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, chlorine, fluorine, bromine, iodine, COOH, carboxylate, amide, nitrile, nitro, sulfonyl, sulfate, sulfone, amino, tethered amino, quaternary amino, imino, and the like, $X^{1'}-X^{4'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, and the like, wherein $W^{2'}$ and $W^{3'}$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^{4'}$ and $W^{5'}$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like.

In another specific embodiment of the above probe set, detectable label is a compound of the formula:

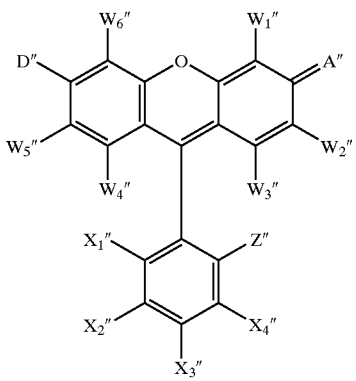

wherein

Z" is COOH, and the like,

A" is O, $N(R^{1"})(R^{2"})$ wherein $R^{1"}$ and $R^{2"}$ are independently lower alkyl, substituted lower alkyl, and the like, D" is OH, $OR^{3"}$ wherein $R^{3"}$ is lower alkyl, substituted lower alkyl, aryl, substituted aryl, and the like, $W^{1"}$ and $W^{6"}$ are independently H, lower alkyl, substituted lower alkyl, COOH, chloro, fluoro, and the like, $W^{2"}$ and $W^{5"}$ are independently H, lower alkyl, substituted lower alkyl, COOH, chloro, fluoro, and the like, $W^{3"}$ and $W^{4"}$ are independently H, lower alky, substituted lower alkyl, COOH, chloro, fluoro, and the like, wherein $W^{2"}$ and $W^{3"}$ may be taken together to form one or more rings comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, and wherein $W^{4"}$ and $W^{5"}$ may be taken together to form a ring comprising 4 to 14 atoms, preferably, 4 to 8 atoms, more preferably, 5 to 7 atoms, usually carbon atoms, and comprising 1 to 7 unsaturations, usually, 1 to 4 unsaturations, such as, e.g., benzo (from benzene), naptho (from naphthalene), anthro (from anthracene), and the like, $X^{1"}-X^{4"}$ are independently H, chloro, fluoro, COOH, bromo, iodo, and the like.

In another specific embodiment of the above probe set, the detectable label is a compound wherein Z" is carboxyl, $W^{6"}$ and $W^{1"}$ are lower alkyl, $W^{5"}$ and $W^{2"}$ are halogen, $X^{2"}$ and $X^{3"}$ are hydrogen or carboxyl and $X^{1"}$ and $X^{4"}$ are hydrogen or halogen.

In another specific embodiment of the above probe set, the detectable label is a compound wherein Z" is carboxyl, $W^{6"}$ and $W^{1"}$ are methyl, $W^{5"}$ and $W^{2"}$ are chloro, one of $X^{2"}$ and $X^{3"}$ are hydrogen and the other is carboxyl and $X^{1"}$ and $X^{4"}$ are hydrogen.

In another specific embodiment of the above probe set, the detectable label is a compound wherein Z" is carboxyl, $W^{6"}$ and $W^{1"}$ are methyl, $W^{5"}$ and $W^{2"}$ are chloro, one of $X^{2"}$ and $X^{3"}$ are hydrogen and the other is carboxyl and $X^{1"}$ and $X^{4"}$ are chloro.

In another specific embodiment of the above probe set, the detectable label is a compound selected from the group of compounds of FIG. 1.

It is noteworthy that some of the compounds mentioned above such as, for example, compounds AMD 001 to AMD 012 as well as FAM (FIG. 10) (charge of −3), have substantially the same spectral properties of excitation wavelength and emission wavelength but have different mass and charge and, thus, different mobilities. By the phrase "substantially the same spectral properties" is meant that the excitation wavelength and the emission wavelength of two compounds are within about 5% of one another, usually, within about 3% of one another, more usually, within about 1% of one another. Accordingly, these compounds are particularly useful as labels in e-tag reagents in situations where the instrumentation employed cannot effectively resolve such compounds on a spectral level. The fact that such compounds have different charge and mass permits their use with one another as the detectable moiety component of the e-tag reagent with the added dimension of differing mobilities. Accordingly, the ability to multiplex determinations using e-tag reagents is expanded.

G. Methods for Use of the E-tags

The methodologies that may be employed involve heterogeneous and homogeneous techniques, where heterogeneous normally involves a separation step, where unbound label is separated from bound label, where homogeneous assays do not require, but may employ, a separation step. One group of assays will involve nucleic acid detection, which includes sequence recognition, snp detection and scoring, transcription analysis, allele determinations, HLA determinations, or other determination associated with variations in sequence. The use of the determination may be forensic, mRNA determinations, mutation determinations, allele determinations, MHC determinations, haplotype determinations, single nucleotide polymorphism determinations, etc. The methodology may include assays dependent on 5'-nuclease activity, as in the use of the polymerase chain reaction or in Invader technology, 3'-nuclease activity, restriction enzymes, or ribonuclease H. All of these methods involving catalytic cleavage of a phosphate linkage, where one to two oligonucleotides are bound to the target template.

Instead of nucleic acid pairing, one may employ specific binding member pairing. There are a large number of specific binding pairs associated with receptors, such as antibodies, poly- and monoclonal, enzymes, surface membrane receptors, lectins, etc., and ligands for the receptors, which may be naturally occurring or synthetic molecules, protein or non-protein, such as drugs, hormones, enzymes, ligands, etc. The specific binding pair has many similarities to the binding of homologous nucleic acids, significant differences being that one normally cannot cycle between the target and the agent and one does not have convenient phosphate bonds to cleave. For heterogeneous assays, the binding of the specific binding pair is employed to separate the bound from the unbound e-tag bonded agents, while with homogeneous assays, the proximity of the specific binding pairs allow for release of the e-tags from the complex. For an inclusive but not exclusive listing of the various manners in which the subject invention may be used, Tables 2 and 3 are provided.

Once the target-binding moiety conjugated with the e-tag has been prepared, it may be used in a number of different assays. The samples may be processed using lysis, nucleic acid separation from proteins and lipids and vice versa, and enrichment of different fractions. For nucleic acid related determinations, the source of the DNA may be any organism, prokaryotic and eukaryotic cells, tissue, environmental samples, etc. The DNA or RNA may be isolated by conventional means, RNA may be reverse transcribed, DNA may be amplified, as with PCR, primers may be used with capture ligands for use in subsequent processing, the DNA may be fragmented using restriction enzymes, specific sequences may be concentrated or removed using homologous sequences bound to a support, or the like. Proteins may be isolated using precipitation, extraction, and chromatography. The proteins may be present as individual proteins or combined in various aggregations, such as organelles, cells, viruses, etc. Once the target components have been preliminarily treated, the sample may then be combined with the e-tag reporter targeted binding proteins.

For a nucleic acid sample, after processing, the probe mixture of e-tags for the target sequences is combined with the sample under hybridization conditions, in conjunction with other reagents, as necessary. Where the reaction is heterogeneous, the target-binding sequence has a capture ligand for binding to a reciprocal binding member for sequestering hybrids to which the e-tag probe is bound. In this case, all of the DNA sample carrying the capture ligand is sequestered, both with and without e-tag reporter labeled probe. After sequestering the sample, non-specifically bound e-tag reporter labeled probe may be removed under a pre-determined stringency based on the probe sequence using washing at an elevated temperature, salt concentration, organic solvent, etc. Then, the e-tag reporter is released into an electrophoretic buffer solution for analysis.

As indicated in Table 2, for amplification one may use thermal cycling. Tables 2 and 3 indicate the properties of binding assays (solution phase e-tag generation followed by separation by CE, HPLC or mass spectra) and multiplexed assays (2–1000) leading to release of a library of e-tags, where every e-tag codes for a unique binding event or assay.

The cleavage of the nucleic acid bound to the template results in a change in the melting temperature of the e-tag residue with release of the e-tag. By appropriate choice of the primer and/or protocol, one can retain the primer bound to the template and the e-tag containing sequence can be cleaved and released from the template to be replaced by an e-tag containing probe.

TABLE 2

Binding and Multiplexed Assays.

| Formats | Recognition Event | Amplification Mode | e-tag Release |
|---|---|---|---|
| Multiplexed assays | Solution hybridization followed by enzyme recognition | PCR, Invader | 5' nuclease 3' nuclease Restriction enzyme Ribonuclease H |
| Sequence recognition for example for multiplexed gene expression, SNP's scoring etc . . . | Solution hybridization followed by channeling | Amplification due to turnover of e-tag binding moiety; OR amplification due to release of multiple e-tags (10 to 100,000) per binding event | Singlet Oxygen ($^1O_2$) Hydrogen Peroxide ($H_2O_2$) Light, energy transfer |
| Patches in microfluidic channels-integrated assay and separation device | Target captured on solid surface; e-tag probe mixture hybridized to target; unbound probes removed; e-tag reporter is released, separated and identified. | Amplification from release of multiple e-tag reporters (10 to 100,000) per probe | Light, enzyme, $^1O_2$, $H_2O_2$, Fluoride, reducing agent, MS, others |

TABLE 3

Immunoassays

| Format | Recognition Event | Amplification Mode | e-tag Release |
|---|---|---|---|
| Proteomics Multiplexed Immunoassays | Sandwich assays Antibody-1 decorated with Sensitizer while antibody-2 is decorated with singlet oxygen cleavable e-tags Competition assays Antibody-1 decorated with Sensitizer while antibody-2 is decorated with singlet oxygen cleavable e-tags | A few (2–10) e-tags released per binding event OR Amplification from release of multiple e-tags (10 to 100,000) per binding event | Singlet Oxygen ($^1O_2$) |
| | Sandwich assays Antibody-1 decorated with Glucose oxidase while antibody-2 is decorated with hydrogen peroxide cleavable e-tags Competition assays Antibody-1 decorated with Glucose oxidase while antibody-2 is decorated with hydrogen peroxide cleavable e-tags | | Hydrogen Peroxide ($H_2O_2$) |
| Patches in microfluidic | Sandwich assays Antibody-1 is | | Light; Enzymes, |

TABLE 3-continued

Immunoassays

| Format | Recognition Event | Amplification Mode | e-tag Release |
|---|---|---|---|
| channels; integrated assay and separation device | attached to a solid surface while antibody-2 is decorated with cleavable e-tags Competition assays Antibody-1 is attached to a solid surface while antibody-2 is decorated with cleavable e-tags | | singlet oxygen, hydrogen peroxide fluoride, reducing agents, mass spectra, others |

The assays may be performed in a competitive mode or a sandwich mode. In the competitive mode, the target competes with a labeled binding member for the reciprocal member. The reciprocal member is bound to the support, either during the complex formation or after, e.g., where an antibody is a specific binding member and anti-immunoglobulin is the reciprocal binding member and is bound to the support. In this mode, the binding sites of the reciprocal binding member become at least partially filled by the target, reducing the number of available binding sites for the labeled reciprocal binding member. Thus, the number of labeled binding members that bind to the reciprocal binding member will be in direct proportion to the number of target molecules present. In the sandwich mode, the target is able to bind at the same time to different binding members; a first support bound member and a second member that binds at a site of the target molecule different from the site at which the support bound member binds. The resulting complex has three components, where the target serves to link the labeled binding member to the support.

In carrying out the assays, the components are combined, usually with the target composition added first and then the labeled members in the competitive mode and in any order in the sandwich mode. Usually, the labeled member in the competitive mode will be equal to at least about 50% of the highest number of target molecules anticipated, preferably at least equal and may be in about 2 to about 10 fold excess or greater. The particular ratio of target molecules to labeled molecules will depend on the binding affinities, the length of time the mixture is incubated, the off rates for the target molecule with its reciprocal binding member, the size of the sample and the like. In the case of the sandwich assays, one will have at least an equal amount of the labeled binding member to the highest expected amount of the target molecules, usually at least about 1.5 fold excess, more usually at least about 2 fold excess and may have about 10 fold excess or more. The components are combined under binding conditions, usually in an aqueous medium, generally at a pH in the range of about 5 to about 10, with buffer at a concentration in the range of about 10 to about 200 mM. These conditions are conventional, where conventional buffers may be used, such as phosphate, carbonate, HEPES, MOPS, Tris, borate, etc., as well as other conventional additives, such as salts, stabilizers, organic solvents, etc.

Usually, the unbound labeled binding member or e-tag probe will be removed by washing the bound labeled binding member. Where particles or beads are employed, these may be separated from the supernatant before washing, by filtration, centrifugation, magnetic separation, etc. After washing, the support may be combined with a liquid into which the e-tag reporters are to be released and/or the functionality of the e-tags is reacted with the detectable label, followed by or preceded by release. Depending on the nature of the cleavable bond and the method of cleavage, the liquid may include reagents for the cleavage. Where reagents for cleavage are not required, the liquid is conveniently an electrophoretic buffer. For example, where the cleavable linkage is photo labile, the support may be irradiated with light of appropriate wavelength to release the e-tag reporters. Where the fluorescent compounds are not present on the e-tags, the e-tags may be reacted with the fluorescent compounds. In some instances the fluorescent compound may be part of the reagent cleaving the cleavable bond, e.g. a disulfide with a thiol. Where there is a plurality of different functionalities on different binding members for reaction with the fluorescent compound, the different fluorescent compounds have functionalities that react with one of the functionalities. The different fluorescent compounds may be added together or individually in a sequential manner. For example, where the functionalities involve thiols, carboxyl groups, aldehydes and olefins, the labels could have activated olefins, alcohols, amines and thiol groups, respectively. By having removable protective groups for one or more of the functionalities, the protective groups may be removed stepwise and the fluorescent compounds added stepwise. In this way cross-reactivity may be avoided. Whether fluorescent compound is present initially or added subsequently is not critical to this invention and is frequently governed by the nature of the target composition, the nature of the labeled binding members, and the nature of the fluorescent compounds. For the most part, it will be a matter of convenience as to the particular method one chooses for providing the fluorescent compound on the e-tag.

Where a reagent is necessary for cleavage, the e-tag reporters may be required to be separated from the reagent solution, where the reagent interferes with the electrophoretic analysis. Depending on the nature of the e-tag reporters and the reagent, one may sequester the e-tag reporters from the reagent by using ion exchange columns, liquid chromatography, an initial electrophoretic separation, and the like. Alternatively, as discussed previously, one may have a capture ligand bound to the e-tag or retained portion of the target-binding region for isolating the e-tag probe, so as to remove any interfering components in the mixture. Once the solution of e-tag reporters is prepared and free of any interfering components, the solution may be analyzed electrophoretically. The analysis may employ capillary electrophoresis devices, microfluidic devices or other devices that can separate a plurality of compounds electrophoretically, providing resolved bands of the individual e-tag reporters.

The protocols for the subject homogeneous assays will follow the procedures for the analogous heterogeneous assays, which may or may not include a releasable e-tag. These protocols employ a signal producing system that includes the label on one of the binding members, the cleavable bond associated with the e-tag, electromagnetic radiation or other reagents involved in the reaction or for diminishing background signal.

Generally, the concentrations of the various agents involved with the signal producing system will vary with the concentration range of the individual analytes in the samples to be analyzed, generally being in the range of about 10 nM to 10 mM. Buffers will ordinarily be employed at a concentration in the range of about 10 to 200 mM. The concentration of each analyte will generally be in the range of about 1 pM to about 100 µM, more usually in the range of about 100 pM to 10 µM. In specific situations the concentrations may be higher or lower, depending on the nature of the analyte, the affinity of the reciprocal binding members, the efficiency of release of the e-tag reporters, the sensitivity with which the e-tags are detected, and the number of analytes, as well as other considerations.

Assays that find use are described in U.S. Pat. Nos. 4,233,402, 5,616,719, 5,807,675, and 6,002,000. The analyte may be combined with one or both reagents. The particular order of addition will vary with the nature of the reagents. Generally, one would prefer to combine the binding reagents and the sample and allow the mixture to incubate, generally at least about 5 min, more usually at least about 15 min, before irradiating the mixture or adding the remaining reagents.

The subject libraries of e-tags may be used to analyze the effect of an agent on a plurality of different compounds. For example, a plurality of substrates may be prepared labeled with an e-tag, where an enzyme catalyzes a reaction resulting in a change in mobility between the product and the starting material. These assays can find use in determining affinity groups or preferred substrates for hydrolases, oxidoreductases, lyases, etc. For example, with kinases and phosphatases, a charged group may be added or removed so as to change the mobility of the product. By preparing a plurality of alcohols or phosphate esters, one can determine which of the compounds serves as a substrate. By labeling the substrates with e-tags, the shift from the substrate to the product may be observed as evidence of the activity of a candidate substrate with the enzyme. By preparing compounds as suicide inhibitors, the enzymes may be sequestered and the e-tag reporters released to define those compounds that may serve as suicide inhibitors and, therefore, preferentially bind to the active site of the enzyme.

The subject methods may also be employed for screening for the activity of one or more candidate compounds, particularly drugs, for their activity against a battery of enzymes. In this situation, active substrates for each of the enzymes to be evaluated may be used, where each of the substrates would have its own e-tag. For those enzymes for which the drug is an inhibitor, the amount of product is diminished in relation to the amount of product in the absence of the candidate compound. In each case the product has a different mobility from the substrate, so that the substrates and products can be readily distinguished by electrophoresis. By appropriate choice of substrates and fluorescent compounds, electropherograms can be obtained showing the effect of the candidate compound on the activity of the different enzymes.

In determinations involving nucleic acids, since snp detection is, for the most part, the most stringent in its requirements, most of the description will be directed toward the multiplexed detection of snp's by way of example and not limitation. For other nucleic acid analyses, frequently the protocols are substantially the same, although in some instances somewhat different protocols may be employed for snp's, because of the greater demands snp's make on fidelity. For proteins, the protocols are substantially different and are described independently of the snp protocols.

Generally, an aqueous medium is employed. Other polar co-solvents may also be employed, usually oxygenated organic solvents of from 1–6, more usually from 1–4, carbon atoms, including alcohols, ethers, formamide and the like. Usually, these co-solvents, if used, are present in less than about 70 weight percent, more usually in less than about 30 weight percent. The temperatures employed are determined by the nature of the assay, the nature of the analytes, the nature of other reagents and so forth. Usually, the temperatures employed are in the range of about 0° C. to about 120° C.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The medium may also contain materials required for enzyme activity such as a divalent metal ion (usually magnesium).

Various ancillary materials will frequently be employed in the methods in accordance with the present invention. For example, in addition to buffers and salts, the medium may also comprise stabilizers for the medium and the reaction components. Frequently, the medium may also include proteins such as albumins, quaternary ammonium salts, polycations such as spermine, surfactants, particularly non-ionic surfactants, binding enhancers, e.g., polyalkylene glycols, or the like.

(4) Analysis of Reaction Products

The separation of the e-tag reporters by electrophoresis can be performed in conventional ways. See, for example, U.S. Pat. Nos. 5,750,015, 5,866,345, 5,935,401, 6,103,199, and 6,110,343, and WO98/5269, and references cited therein. Also, the sample can be prepared for mass spectrometry in conventional ways. See, for example, U.S. Pat. Nos. 5,965,363, 6,043,031, 6,057,543, and 6,111,251.

The presence of each of the cleaved e-tags is determined by the fluorescent compound. The separation of the mixture of labeled e-tag reporters is typically carried out by electroseparation, which involves the separation of components in a liquid by application of an electric field, preferably, by electrokinesis (electrokinetic flow) electrophoretic flow, or electroosmotic flow, or combinations thereof, with the separation of the e-tag reporter mixture into individual fractions or bands. Electroseparation involves the migration and separation of molecules in an electric field based on differences in mobility. Various forms of electroseparation include, by way of example and not limitation, free zone electrophoresis, gel electrophoresis, isoelectric focusing and isotachophoresis. Capillary electroseparation involves electroseparation, preferably by electrokinetic flow, including electrophoretic, dielectrophoretic and/or electroosmotic flow, conducted in a tube or channel of about 1–200 micrometer, usually, about 10–100 micrometers cross-sectional dimensions. The capillary may be a long independent capillary tube or a channel in a wafer or film comprised of silicon, quartz, glass or plastic.

Suitable detectors for use in detection zones include, by way of example, photomultiplier tubes, photodiodes, photodiode arrays, avalanche photodiodes, linear and array charge coupled device (CCD) chips, CCD camera modules, spectrofluorometers, and the like. Excitation sources include, for example, filtered lamps, LED's, laser diodes, gas, liquid and solid-state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. Nos. 5,560,811

(column 11, lines 19–30), 4,675,300, 4,274,240 and 5,324, 401, the relevant disclosures of which are incorporated herein by reference.

H. Kits for Use of the E-tag Technology

As a matter of convenience, predetermined amounts of reagents employed in the present invention can be provided in a kit in packaged combination. One exemplary kit is for use in detecting the presence and/or amount of each and any of a plurality of bivalent target molecules. The kit comprises in packaged combination a first binding agent capable of binding to a first binding site on the target molecules, and a plurality of second binding agents, each capable of target-specific binding to a second binding site on a selected target. Each of the second binding agents has a unique cleavable reporter group that includes a cleavable moiety that is susceptible to cleavage, and an electrophoretic tag. The tags differ among the second binding agents by virtue of a modification that imparts a unique mobility. The electrophoretic tag in at least one of the second binding agents comprises a fluorescent compound of the formula described above. In one embodiment the first binding agent and the second binding agents are polynucleotides for detecting each and any of a plurality of target DNA sequences. In another embodiment the first binding agent and the second binding agents are polypeptides for detecting each and any of a plurality of target polypeptides. The kit may comprise sets of electrophoretic tag probes.

The kit may further comprise a device for conducting capillary electrophoresis as well as a template dependent polynucleotide polymerase having 5' to 3' exonuclease activity. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. For example, the dNTPs, the oligonucleotide pairs, optionally the polymerase, may be included in a single container, which may also include an appropriate amount of buffer. The kits may also include a written description of a method in accordance with the present invention as described above.

In another embodiment of a kit, the electrophoretic tag is a fluorescent conjugate represented by the formula:

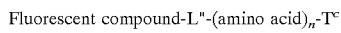

wherein L" is a bond or a linking group of from 1 to 20 atoms in the chain and n is 1 to 100. The fluorescent compound may be one described above, the amino acid may be lysine and L" may be a bond in the form of an amide linkage involving a meta-carboxyl of the fluorescent compound and the terminal amine group of lysine, and $T^c$ is the OH of the carboxyl of the last amino acid, a moiety of from 0 to 6 carbon atoms for linking the carboxy to a nucleoside, nucleotide or nucleotide triphosphate.

In another embodiment of a kit in accordance with the invention, the electrophoretic tag is a label conjugate represented by the formula:

wherein X is selected from the group consisting of: OH, NH-lysine, NH-(lysine)$_2$, NH-alanine, NH-aspartic acid, NH-(aspartic acid)$_2$, NH-(aspartic acid)$_3$, NH-(aspartic acid)$_4$, NH-(aspartic acid)$_5$, NH-(aspartic acid)$_6$, NH-(aspartic acid)$_7$, NH-alanine-lysine, NH-aspartic acid-lysine, NH-(aspartic acid)$_2$-lysine, NH-(aspartic acid)$_3$-lysine, NH-(aspartic acid)$_4$-lysine, NH-(aspartic acid)$_5$-lysine, NH-(aspartic acid)$_6$-lysine, NH-(aspartic acid)$_7$-lysine, NH-(aspartic acid)$_8$-lysine, NH-(lysine)$_4$, and NH-(lysine)$_5$. The terminal carboxy may be linked to $T^c$.

The e-tags described above may terminate in an appropriate functionality for linking to a nucleotide, nucleotide triphosphate, or other molecule of interest, or may terminate in such moieties.

The kits will include at least two detectable regions and sufficient reagents to have at least 10, usually at least 20 and frequently at least 50 or more different e-tag reporters that can be separated by their mobility.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, oligonucleotides and peptides used in the following examples were prepared by synthesis using an automated synthesizer and were purified by gel electrophoresis or HPLC.

The following abbreviations have the meanings set forth below:

Tris HCl-Tris(hydroxymethyl)aminomethane-HCl (a 10× solution) from Bio Whittaker, Walkersville, Md.

HPLC—high performance liquid chromatography

BSA—bovine serum albumin from Sigma Chemical Company, St. Louis, Mo.

EDTA—ethylene diamine tetra-acetate from Sigma Chemical Company bp—base pairs g—grams mM—millimolar TET—tetrachlorofluorescein FAM—fluorescein TAMRA—tetramethyl rhodamine EOF—electroosmotic flow Reagents All reagents were synthesized as described below or purchased from Aldrich Chemical Company, Milwaukee, Wis., with the exception of 6-carboxyfluorescein, which was purchased from Molecular Probes, Eugene, Oreg., and 2-cyanoethyl diisopropylchlorophosphoramidite, which was purchased from Chem Genes, Ashland, Mass.

Example 1

Synthesis of AMD 001

Into a 250 mL round bottom flask was placed 2-methyl resorcinol (6.46 g, 52.0 mmol) and trimellitic anhydride (5.0 g, 26.0 mmol). Methanesulfonic acid (50 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine precipitate was filtered and dried to afford AMD001 (2.0 g, 90%). Mass (LR ES−) calculated for $C_{23}H_{16}O_7$ 404, found: 403 (M−H+).

Example 2
Synthesis of AMD 002

Into a 50 mL round bottom flask was put 4-chlororesorcinol (1.5 g, 10.4 mmol), trimellitic anhydride (1.0 g, 5.2 mmol), and zinc chloride (0.36 g, 2.6 mmol). This mixture of solids was heated to 175° C. using an oil bath. At elevated temperatures all materials liquefied and subsequently turned dark in color. After allowing the reaction to stir for 30 min, the solution was cooled to room temperature and then dissolved in a 15% NaOH solution. The dark red solution was acidified with a 50% HCl solution which resulted in the formation of an orange solid which was filtered and dried to yield AMD002 (1.4 g, 60%). Mass (LR ES−) calculated for $C_{21}H_{10}Cl_2O_7$ 544, found: 543 (M−H+).

Example 3
Synthesis of AMD 003

Into a 50 mL round bottom flask was put 4-ethyl resorcinol (1.44 g, 10.4 mmol) and trimellitic anhydride (1.0 g, 5.2 mmol). Methanesulfonic acid (10 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine orange precipitate was filtered and dried to afford AMD003 (2.0 g, 87%). Mass (LR ES−) calculated for $C_{25}H_{20}O_7$ 432, found: 431 (M−H+). Mass (LR ES−) calculated for $C_{21}H_{10}Cl_2O_7$ 544, found: 543 (M−H+).

Example 4
Synthesis of AMD 004

Into a 100 mL round bottom flask was put 4-hexylresorcinol (2.0 g, 10.4 mmol) and trimellitic anhydride (1.0 g, 5.2 mmol). Methanesulfonic acid (15 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine orange precipitate was filtered and dried to afford AMD004 (2.2 g, 78%). Mass (LR ES−) calculated for $C_{33}H_{36}O_7$ 544, found: 543 (M−H+).

Example 5
Synthesis of AMD 005

Into a 50 mL round bottom flask was put 2,4-dihydroxybenzoic acid (1.6 g, 10.4 mmol) and trimellitic anhydride (1.0 g, 5.2 mmol). Methanesulfonic acid (10 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine orange precipitate was filtered and dried to afford AMD005 (2.1 g, 88%). Mass (LR ES−) calculated for $C_{23}H_{12}O_{11}$ 464, found: 463 (M−H+).

Example 6
Synthesis of AMD 006

Into a 50 mL round bottom flask was put 2,6-dihydroxybenzoic acid (1.6 g, 10.4 mmol) and trimellitic anhydride (1.0 g, 5.2 mmol). Methanesulfonic acid (10 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine orange precipitate was filtered and dried to afford AMD006 (2.3 g, 96%). Mass (LR ES−) calculated for $C_{23}H_{12}O_{11}$ 464, found: 463 (M−H+).

Example 7
Synthesis of AMD 007

Into a 50 mL round bottom flask was put 2,5-dimethylresorcinol (1.0 g, 7.24 mmol) and trimellitic anhydride (0.7 g, 3.6 mmol). Methanesulfonic acid (10 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine orange precipitate was filtered and dried to afford AMD007 (0.65 g, 42%). Mass (LR ES−) calculated for $C_{25}H_{20}O_7$ 432, found: 431 (M−H+).

Example 8
Synthesis of AMD 008

Synthesis of 2,4-dihydroxy-2',4' or 5'-dicarboxybenzophenone—Into a 50 mL round bottom flask was put 5(6)-carboxyfluorescein (10 g, 26.6 mmol) and 10 mL of water containing 18 g of sodium hydroxide. The suspension was heated to 175° C. in an oil bath for 2 hours then diluted with 50 ml of water and allowed to cool to room temperature. Acidification with concentrated hydrochloric acid precipitated the product as a tan solid (7 g, 93%).

Into a 25 mL pear bottom flask was put 1,3-dihydroxynaphthalene (0.5 g, 3.12 mmol) and 2,4-dihydroxy-2',4' or 5'-dicarboxybenzophenone (0.9 g, 3.12 mmol) (prepared as described above). Methanesulfonic acid (5 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (50 mL). The resulting fine dark precipitate was filtered and dried to afford AMD 008 (0.2 g, 13%). Mass (LR ES−) calculated for $C_{25}H_{14}O_7$ 426, found: 425 (M−H+).

Example 9
Synthesis of AMD 009

Into a 25 mL round bottom flask was put 4-chlororesorcinol (0.18 g, 1.27 mmol) (prepared as described above) and 2,4-dihydroxy-2',4' or 5'-dicarboxybenzophenone (0.36 g, 1.27 mmol). (1.0 g, 5.2 mmol). Methanesulfonic acid (5 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (50 mL). The resulting fine dark precipitate was filtered and dried to afford AMD 009 (0.05 g, 10%). Mass (LR ES−) calculated for $C_{21}H_{11}ClO_7$ 410, found: 409 (M−H+).

Example 10
Synthesis of AMD 012

Into a 10 mL round bottom flask was put 1,3-dihydroxynaphthalene (0.17 g, 1.04 mmol) and trimellitic anhydride (0.1 g, 3.5 mmol). Methanesulfonic acid (2 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (10 mL). The resulting dark precipitate was filtered and dried to afford AMD 012 (0.05 g, 20%). Mass (LR ES⁻) calculated for $C_{29}H_{16}O_7$ 476, found: 475 (M−H+).

Example 11
Synthesis of AMD-S 001

Synthesis of 2-methyl-4-chlororesorcinol—The reaction scheme for this synthesis is depicted in FIG. 5. Into a 500 mL round bottom flask was put 2-methylresorcinol (10.0 g, 80.6 mmol) and diethyl ether (150 mL). This solution was stirred under an atmosphere of nitrogen and cooled to 0° C. with an ice/methanol bath. Sulfuryl chloride was dissolved in 50 mL of diethyl ether and added dropwise from an addition funnel over a period of one hour. After complete addition, the solution was allowed to warm to room temperature and stirring was continued for three hours. The reaction was neutralized with a saturated solution of sodium bicarbonate, the organic phase washed with water (2×100 mL) then brine (2×100 mL) and dried over $Na_2SO_4$, filtered, and concentrated in vacuo to yield a yellow oil. On standing, this set up to light brown crystals of 2-methyl-4-chlororesorcinol (10 g, 78%).

Synthesis of dichlorodimethylfluorescein (AMD-S 001)—The reaction scheme for this synthesis is depicted in FIGS. 5–6. Into a 50 mL round bottom flask was put 2-methyl-4-chlororesorcinol (1.66 g, 10.4 mmol), trimellitic anhydride (1.0 g, 5.2 mmol), and zinc chloride (0.36 g, 2.6 mmol). This mixture of solids was heated to 175° C. using an oil bath. At elevated temperatures all materials liquefied and subsequently turned dark in color. After allowing the reaction to stir for 30 min, the solution was cooled to room temperature and then dissolved in a 15% NaOH solution. The dark red solution was acidified with a 50% HCl solution, which resulted in the formation of an orange solid which was filtered and dried to yield AMD-S 001 (1.3 g, 52%). Mass (LR ES⁻) calculated for $C_{23}H_{14}Cl_2O_7$ 472, found: 471 (M−H+).

Example 12
Synthesis of AMD-S 002

Figure 7:
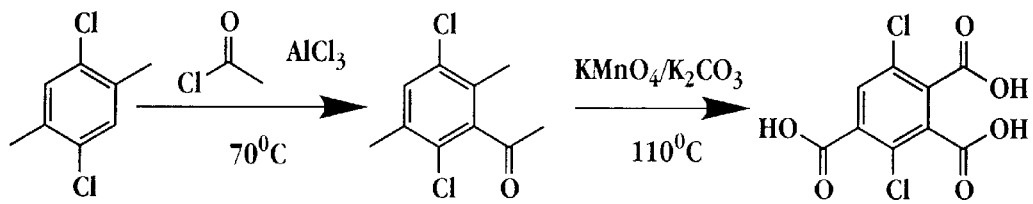
FIG. 7 depicts one approach to the synthesis of dichlorotrimellitic acid.

Synthesis of dichlorotrimellitic acid—The reaction scheme for this synthesis is depicted in FIG. 7. Into a 250 ml round bottom flask was put 2,5-dichloroxylene (5 g, 28.6 mmol) and aluminum chloride (4.6 g, 34.3 mmol). Solids were thoroughly mixed, then acetyl chloride (2.0 mL, 28.6 mmol) was added and the reaction immersed in an oil bath at 70° C. After cessation of gas evolution (approx 30 min), reaction was allowed to cool to room temperature and partitioned between ethyl acetate (100 mL) and water (200 mL). The organic layer was dried over $Na_2SO_4$, filtered, and concentrated in vacuo to yield 5 g of 6-acetyl-2,5-dichloroxylene as a yellow oil. This crude was used directly for the subsequent oxidation without purification.

Into a 250 mL round bottom flask was put 6-acetyl-2,5-dichloroxylene (5 g) and 100 mL of a 10% solution of potassium carbonate containing 18 g of potassium permanganate. This was heated to 110° C. in an oil bath for 4 hours, after which time it was cooled to room temperature and poured into 6N H2SO4. Manganese dioxide settled out of solution, but was not filtered. Aqueous phase was extracted with diethyl ether (3×100 mL) and the pooled extracts washed once with brine (200 ml), dried over $Na_2SO_4$, filtered, and concentrated in vacuo to yield dichlorotrimellitic acid (2.92 g, 37% overall) as a white solid. Mass (LR ES⁻) calculated for $C_9H_4Cl_2O_6$ 278, found: 277 (M−H+), 555 (2M−H+).

Figure 8:
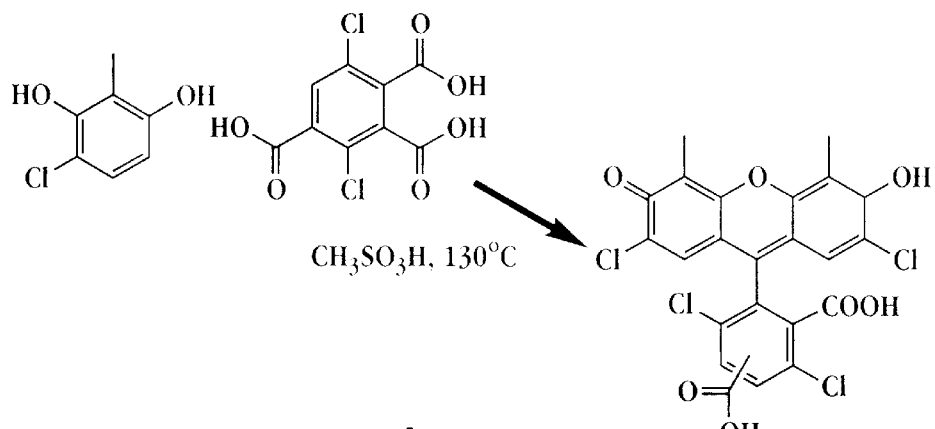
FIG. 8 depicts one approach to the synthesis of AMD-S 002.
Figure 9:
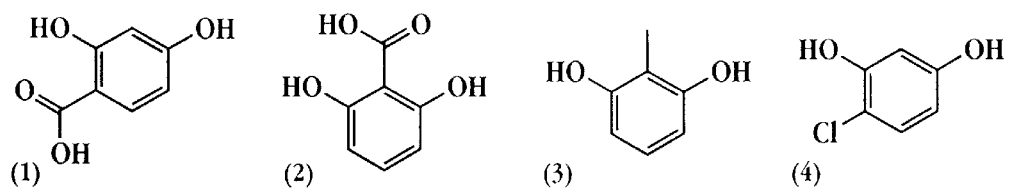
FIG. 9 depicts examples of resorcinols that may be used in the synthesis of fluorescent compounds employed in the invention.
Figure 9:
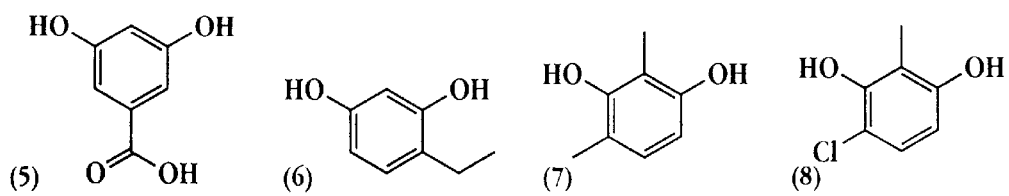
Figure 9:
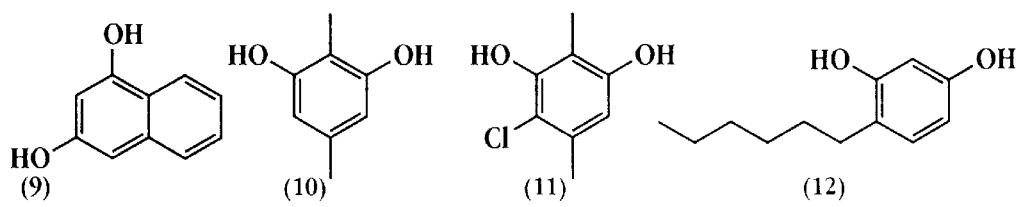

Synthesis of tetrachlorodimethylfluorescein (AMD-S 002)—The reaction scheme for this synthesis is depicted in FIG. 8. Into a 50 mL round bottom flask was put 2-methyl-4-chlororesorcinol (2.84 g, 17.9 mmol) (prepared as described above), and 2,5-dichlorotrimellitic acid (2.5 g, 9.0 mmol) (prepared as described above). Methanesulfonic acid (15 mL) was then added and the resulting suspension was heated to 130° C. using an oil bath. At elevated temperatures all materials went into solution, which subsequently turned dark in color. After allowing the reaction to stir for 30 min, the solution was cooled to room temperature and then added dropwise to rapidly stirring water (100 mL). The resulting fine red precipitate was filtered and dried to afford AMD-S 002 (4.5 g, 90%). Mass (LR ES⁻) calculated for $C_{23}H_{12}Cl_4O_7$ 540, found: 539 (M−H+).

Example 13
Isolation of Fluorescein Derivatives

A. General Procedure for the Isolation of 6-carboxyfluorescein Derivatives

Fluorescein derivatives, prepared as a mixture of 5(6) isomers, were added to 100 equivalents of acetic anhydride and 4 equivalents of pyridine. This solution was heated briefly and monitored by TLC 45:45:10 (Hxn:EtoAc:MeOH) for the formation of the diacetyl derivative. After complete conversion, the solution was stored at 4° C. overnight to precipitate the 6-carboxy pyridinium salt, which was filtered and washed with additional acetic anhydride. This diacetyl salt was converted back to the free fluorescein derivative by treatment with ammonia in methanol.

B. Isolation of 6-carboxydichlorodimethylfluorescein

Into a 50 mL round bottom flask was put 5(6)-carboxy dichlorodimethylfluorescein (1 g, 2.1 mmol), acetic anhydride (19.8 mL, 210 mmol), and pyridine (0.681 mL, 8.4 mmol). Heated to 100° C. in an oil bath for 10 minutes then stored at 4° C. overnight. Precipitate which had formed was filtered and washed with 5 mL cold acetic anhydride. This off white salt (465 mg) was suspended in 1 mL of methanol and added to 2 mL of a 7N solution of ammonia in methanol. The salt immediately dissolved and the solution became dark orange in color. Evaporation of solvent and recrystallization of the residue from methanol gave 200 mg of 6-carboxy dichlorodimethylfluorescein a crimson red solid.

Example 14
Synthesis of Elements of E-tag Probes

A. Synthesis of 6-Carboxyfluorescein Phosphoramidite Derivatives

To a solution of 6-carboxyfluorescein (6-FAM) (0.5 g, 1.32 mmol) in dry pyridine (5 mL) was added drop wise, isobutyric anhydride (0.55 mL, 3.3 mmol). The reaction was allowed to stir at room temperature under an atmosphere of nitrogen for 3 h. After removal of pyridine in vacuo the residue was redissolved in ethyl acetate (150 mL) and washed with water (150 mL). The organic layer was separated, dried over $Na_2SO_4$, filtered, and concentrated in vacuo to yield a brownish residue. This material was dissolved in $CH_2Cl_2$ (5 mL) after which N-hydroxy succinimide (0.23 g, 2.0 mmol) and dicyclohexylcarbodiimide (0.41 g, 1.32 mmol) were added. The reaction was allowed to stir at room temperature for 3 h and then filtered through a fritted funnel to remove the white solid, which had formed. To the filtrate was added aminoethanol (0.12 mL, 2.0 mmol) dissolved in 1 mL of $CH_2Cl_2$. After 3 h the reaction was again filtered to remove a solid that had formed, and then diluted with additional $CH_2Cl_2$ (50 mL). The solution was washed with water (150 mL) and then separated. The organic layer was dried over $Na_2SO_4$, filtered, and concentrated in vacuo to yield a white foam (0.7 g, 95%, 3 steps). $^1H$ NMR: (DMSO), 8.68 (t, 1H), 8.21 (d, 1H), 8.14 (d, 1H), 7.83 (s, 1H), 7.31 (s, 2H), 6.95 (s, 4H), 4.69 (t, 1H), 3.45 (q, 2H), 3.25 (q, 2H), 2.84 (h, 2H), 1.25 (d, 12 H). Mass (LR FAB$^+$) calculated for $C_{31}H_{29}NO_9(M+H^+)$ 559.2, found: 560.

B. Synthesis of Modified Fluorescein Phosphoramidites

Pivaloyl protected carboxyfluorescein: Into a 50 mL round bottom flask was placed 5(6)-carboxyfluorescein (0.94 g, 2.5 mmol), potassium carbonate (1.0 g, 7.5 mmol) and 20 mL of dry DMF. The reaction was stirred under nitrogen for 10 min, after which trimethylacetic anhydride (1.1 mL, 5.5 mmol) was added via syringe. The reaction was stirred at room temperature overnight, and then filtered to remove excess potassium carbonate and finally poured into 50 mL of 10% HCl. A sticky yellow solid precipitated out of solution. The aqueous solution was decanted off and the residual solid was dissolved in 10 mL of methanol. Drop wise addition of this solution to 10% HCl yielded a fine yellow precipitate, which was filtered and air dried to yield an off white solid (0.88 g, 62%). TLC (45:45:10 of Hxn:EtOAc:MeOH).

NHS ester of protected pivaloyl carboxyfluorescein. Into a 200 mL round bottom flask was placed the protected carboxyfluorescein (2.77 g, 5.1 mmol) and 50 mL of dichloromethane. N-hydroxysuccinimide (0.88 g, 7.6 mmol) and dicyclohexylcarbodiimide (1.57 g, 7.6 mmol) were added and the reaction was stirred at room temperature for 3 hours. The reaction was then filtered to remove the precipitated dicyclohexyl urea byproduct and reduced to approx. 10 mL of solvent in vacuo. Drop wise addition of hexanes with cooling produced a yellow-orange colored solid, which was triturated with hexanes, filtered and air-dried to yield 3.17 g (95%) of product. TLC (45:45:10 of Hxn:EtOAc:MeOH).

Alcohol. Into a 100 mL round bottom flask was placed the NHS ester (0.86 g, 1.34 mmol) and 25 mL of dichloromethane. The solution was stirred under nitrogen after which aminoethanol (81 mL, 1 eq) was added via syringe. The reaction was monitored by TLC (45:45:10 Hxn, EtOAc, MeOH) and was found to be complete after 10 min. The dichloromethane was then removed in vacuo and the residue dissolved in EtOAc, filtered and absorbed onto 1 g of silica gel. This was bedded onto a 50 g silica column and eluted with Hxn:EtOAc:MeOH (9:9:1) to give 125 mg (20%) of clean product.

Phosphoramidite. Into a 10 mL round bottom flask containing 125 mg of the alcohol was added 5 mL of dichloromethane. Diisopropyl ethylamine (139 µL, 0.8 mmol) was added via syringe. The colorless solution turned bright yellow. 2-cyanoethyl diisopropylchlorophosphoramidite (81 µL, 0.34 mmol) was added via syringe and the solution immediately went colorless. After 1 hour TLC (45:45:10 of Hxn:EtOAc:TEA) showed the reaction was complete with the formation of two closely eluting isomers. Material was purified on a silica column (45:45:10 of Hxn:EtOAc:TEA) isolating both isomers together and yielding 130 mg (85%).

Carboxylic acid. Into a 4 mL vial was placed 12-aminododecanoic acid (0.1 g, 0.5 mmol) and 2 mL of pyridine. To this suspension was added chlorotrimethyl silane (69 µL, 1.1 eq) via syringe. After all material dissolved (10 min) NHS ester (210 mg, 0.66 eq) was added. The reaction was stirred at room temperature overnight and then poured into water to precipitate a yellow solid, which was filtered, washed with water, and air-dried. TLC (45:45:10 of Hxn:EtOAc:MeOH) shows a mixture of two isomers.

General Procedure for Remaining Syntheses. The carboxylic acid formed as described above is activated by NHS ester formation with 1.5 eq each of N-hydroxysuccinimide and dicyclohexylcarbodiimide in dichloromethane. After filtration of the resulting dicyclohexylurea, treatment with 1 eq of varying amino alcohols will effect amide bond formation and result in a terminal alcohol. Phosphitylation using standard conditions described above will provide the phosphoramidite.

C. Synthesis on an ABI 394 DNA Synthesizer

6-Carboxyfluorescein (6-FAM) phosphoramidite is prepared by the addition of 2.96 ml of anhydrous acetonitrile to a 0.25 gram bottle of the fluorescein phosphoramidite, to give a 0.1 M solution. The bottle is then loaded onto the ABI 394 DNA synthesizer at position 8 using the standard bottle change protocol. The other natural [$dA^{bz}$ (0.1 M: 0.25 g/2.91 mL anhydrous acetonitrile), $dC^{Ac}$(0.1 M: 0.25 g/3.24 mL anhydrous acetonitrile), dT(0.1 M: 0.25 g/3.36 mL anhydrous acetonitrile), $dG^{dmf}$ (0.1 M: 0.25 g/2.81 mL anhydrous acetonitrile)] phosphoramidite monomers are loaded in a similar fashion to ports 1–4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols.

Standard Reagents Employed for DNA Synthesis

Oxidizer: 0.02 M Iodine (0.015 M for MGB Probes)

DeBlock: 3% trichloracetic acid in dichloromethane

Activator: 1H-Tetrazole in anhydrous acetonitrile

HPLC Grade Acetonitrile (0.002% water)

Cap A: acetic anhydride

Cap B: N-methyl imidazole

The target sequence of interest is then input with a terminal coupling from port 8 to attach ACLA 001 to the 5'-end of the sequence. A modified cycle is then chosen such that the desired scale (0.2 µmol, 1.0 µmol, etc.) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing e-tag reporters have been synthesized on various standard 500 Å CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis, the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

D. Synthesis of Phosphoramidites of AMD-S001 and AMD-S002

The phosphoramidites of AMD-S001 and AMD-S002 were synthesized in a manner similar to that described above for the synthesis of the phosphoramidite of 6-FAM.

Figure 10:
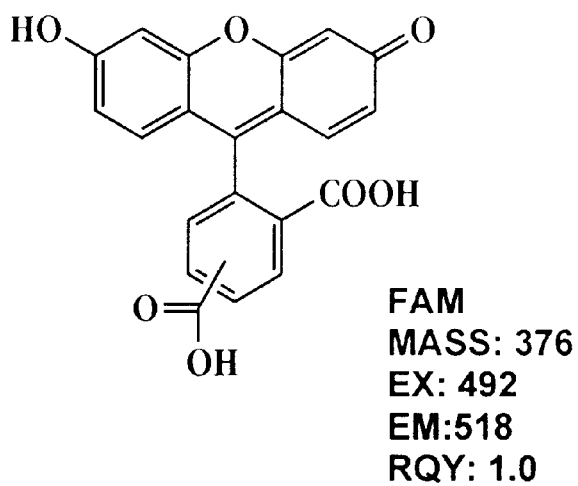
FIG. 10 depicts FAM.
Figure 11:
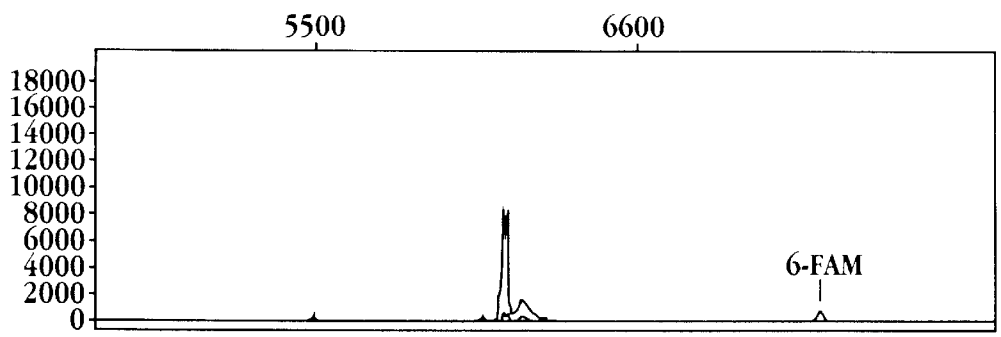
FIG. 11 depicts an electropherogram of 6-FAM.
Figure 12:
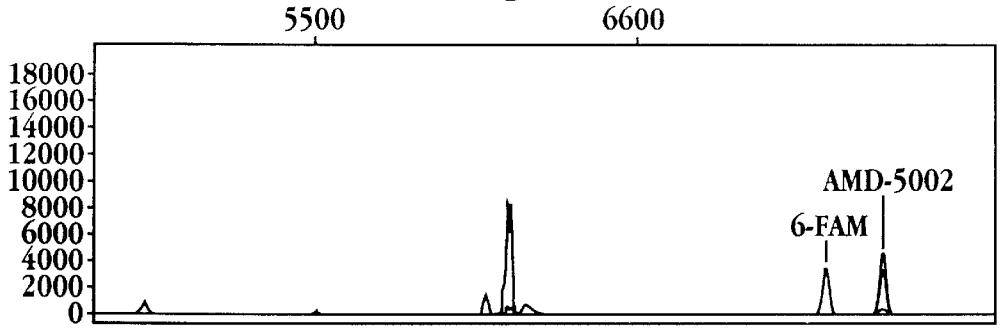
FIG. 12 depicts an electropherogram of 6-FAM and AMD-S 002.
Figure 13:
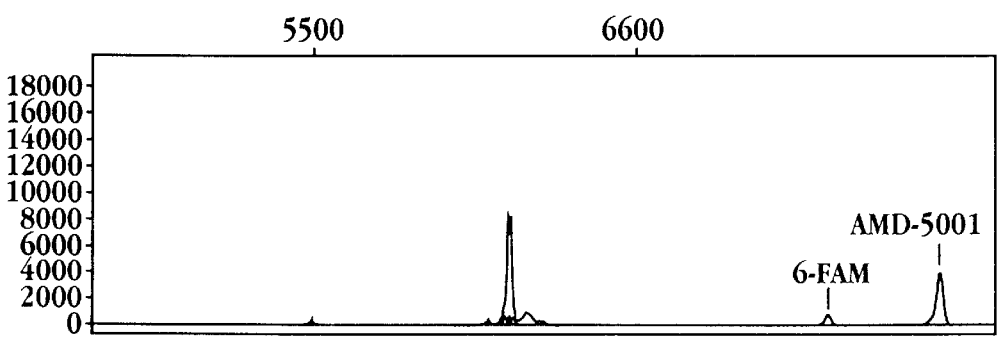
FIG. 13 depicts an electropherogram of 6-FAM and AMD-S 001.

Example 15
Electroseparation of Fluorescent Compound Conjugates on Microfluidic Chip Phosphoramidites comprising AMD-S001 and AMD-S002 and 6-FAM prepared as described above were combined in an aqueous buffered solution and were separated and detected in an electrophoresis chip. Detection was 0.5 cm for the injection point on the anodal side of an electrophoresis channel. The results are shown in FIG. 10 (6-FAM alone), FIG. 11 (6-FAM and AMD-S001) and FIG. 12 (6-FAM and AMD-S002).

It is evident from the above results that the subject inventions provide powerful ways of preparing compositions for use in multiplexed determinations and methods for performing multiplexed determinations using such compositions. The methods provide for homogeneous and heterogeneous protocols, both with nucleic acids and proteins, as exemplary of other classes of compounds. It is further evident from the above results that the subject invention provides an accurate, efficient and sensitive process, as well as compositions for use in the process, to perform multiplexed reactions. The protocols provide for great flexibility in the manner in which determinations are carried out and maybe applied to a wide variety of situations involving haptens, antigens, nucleic acids, cells, etc., where one may simultaneously perform a number of determinations on a single or plurality of samples and interrogate the samples for a plurality of events. The results of the determination are readily read in a simple manner using electrophoresis or mass spectrometry. Systems are provided where the entire process, after addition of the sample and reagents, may be performed under the control of a data processor with the results automatically recorded.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

It is claimed:

1. A probe set for detecting the presence or absence of one or more target compounds, the probe set comprising a plurality of electrophoretic probes selected from the group defined by the formula:

$$[(D, M)-L]_k-T$$

wherein:
T is a target-binding moiety specific for a target compound;
k is an integer greater than or equal to one;
L is a cleavable linkage that is cleaved by oxidation by an active species;
D is a detection group; and
M is a mobility modifier consisting of from 1 to 200 atoms other than hydrogen selected from the group consisting of carbon, oxygen, sulfur, nitrogen, phosphorus, and boron;

wherein, upon cleavage of L, an eTag reporter comprising a detection group, D, and a mobility modifier, M, is produce having a molecular weight in the range of from 150 to 10,000 daltons and a distinct charge/mass ratio so that eTag reporters from different electrophoretic probes form resolved bands upon electrophoretic separation; and wherein detection group, D, is a fluorescent molecule selected from the group defined by the formula:

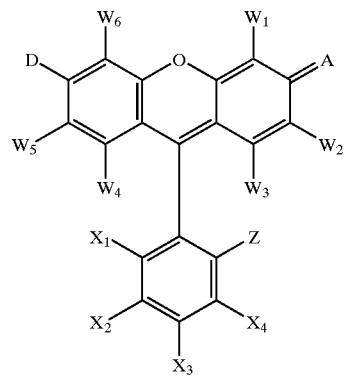

wherein:
Z is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, imino, phosphorus containing species, or polymer chains of from about 2 to about 10 monomer units, A is O, $N^+(R^1)(R^2)$ wherein $R^1$ and R2 are independently H, lower alkyl, or substituted lower alkyl, D is OH, $OR^3$ wherein $R^3$ is lower alkyl, substituted lower alkyl, aryl, substituted aryl, $N(R^1)(R^2)$ wherein $R^1$ and $R^2$ are independently H, lower alkyl, or substituted lower alkyl, $W^1$, $W^2$, $W^3$, $W^4$, $W^5$ and $W^6$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, or imino, $X^1$-$X^4$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, or imino, wherein $W^2$ and $W^3$ may be taken together to form one or more rings comprising 4 to 14 atoms and comprising 1 to 7 unsaturations, and wherein $W^4$ and $W^5$ may be taken together to form a ring comprising 4 to 14 atoms and comprising 1 to 7 unsaturations.

2. The probe set of claim 1 wherein said cleavable linkage is selected from the group consisting of olefins, thioethers, sulfoxides, and selenium analogs of thioethers or sulfoxides.

3. The probe set of claim 2 wherein said active species is selected from the group consisting of singlet oxygen, hydrogen peroxide, NADH, and hydroxyl radicals.

4. The probe set of claim 3 wherein said target-binding moiety is a monoclonal antibody or a polyclonal antibody.

5. The probe set of claim 4 wherein k is in the range of from 1 to 20.

6. The probe set according to claim 1, 2, 3, 4 or 5 wherein said plurality is in the range of from 5 to 100.

7. The probe set according to claim 6 wherein each said detection group, D, of each electrophoretic probe has substantially the same spectral properties.

8. The probe set of claim 6 wherein said fluorescent molecule is selected from a group defined by the formula:

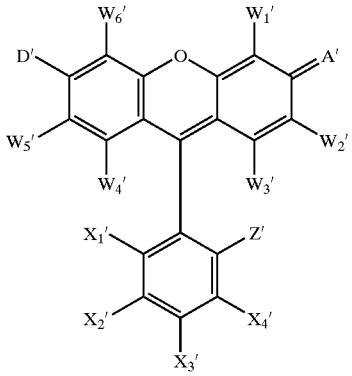

wherein:

Z' is COOH,

A' is O,

D' is OH, $OR^{3'}$ wherein $R^{3'}$ is lower alkyl, substituted lower alkyl, aryl, or substituted aryl, $W^{1'}$, $W^{2'}$, $W^{3'}$, $W^{4'}$ and $W^{6'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromide, iodine, COOH, carboxylate, amide, nitrile, nitro, sulfonyl, sulfate, sulfone, amino, tethered amino, quaternary amino, or imino, $W^{5'}$ is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, chlorine, fluorine, bromine, iodine, COOH, carboxylate, amide, nitrile, nitro, sulfonyl, sulfate, sulfone, amino, tethered amino, quaternary amino, or imino, $X^{1'}-X^{4'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, or imino, wherein $W^{2'}$ and $W^{3'}$ may be taken together to form one or more rings comprising 4 to 14 atoms and comprising 1 to 7 unsaturations, and wherein $W^{4'}$ and $W^{5'}$ may be taken together to form a ring comprising 4 to 14 atoms and comprising 1 to 7 unsaturations.

9. The probe set of claim 6 wherein said fluorescent molecule is selected from the group defined by the formula:

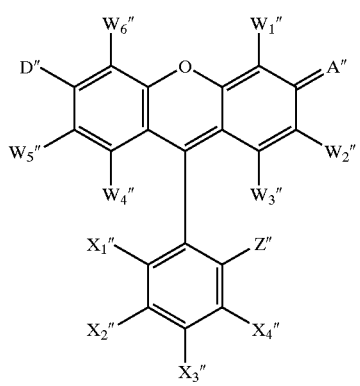

wherein

Z" is COOH,

A" is $N(R^{1"})(R^{2"})$ wherein $R^{1"}$ and $R^{2"}$ are independently lower alkyl, or substituted lower alkyl, D" is OH, $OR^{3'}$ wherein $R^{3'}$ is lower alkyl, substituted lower alkyl, aryl, or substituted aryl, $W^{1"}$ and $W^{6"}$ are independently H, lower alkyl, substituted lower alkyl, COOH, chloro, or fluoro, $W^{2"}$ and $W^{5"}$ are independently H, lower alkyl, substituted lower alkyl, COOH, chloro, or fluoro, $W^{3"}$ and $W^{4"}$ are independently H, lower alkyl, substituted lower alkyl, COOH, chloro, or fluoro, wherein $W^{2"}$ and $W^{3"}$ may be taken together to form one or more rings comprising 4 to 14 atoms and comprising 1 to 7 unsaturations, and wherein $W^{4"}$ and $W^{5"}$ may be taken together to form a ring comprising 4 to 14 atoms and comprising 1 to 7 unsaturations, $X^{1"}-X^{4"}$ are independently H, chloro, fluoro, COOH, bromo, or iodo.

10. The probe set of claim 9 wherein Z" is carboxyl, $W^{6"}$ and $W^{1"}$ are lower alkyl, $W^{5"}$ and $W^{2"}$ are halogen, $X^{2"}$ and $X^{3"}$ are hydrogen or carboxyl and $X^{1"}$ and $X^{4"}$ are hydrogen or halogen.

11. The probe set of claim 9 wherein Z" is carboxyl, $W^{6"}$ and $W^{1"}$ are methyl, $W^{5"}$ and $W^{2"}$ are chloro, one of $X^{2"}$ and $X^{3"}$ are hydrogen and the other is carboxyl and $X^{1"}$ and $X^{4"}$ are hydrogen.

12. The probe set of claim 9 wherein Z" is carboxyl, $W^{6"}$ and $W^{1"}$ are methyl, $W^{5"}$ and $W^{2"}$ are chloro, one of $X^{2"}$ and $X^{3"}$ are hydrogen and the other is carboxyl and $X^{1"}$ and $X^{4"}$ are chloro.

13. The probe set of claim 1 wherein k is in the range of from 1 to 20.

14. The probe set according to claim 13 wherein said plurality is in the range of from 5 to 100.

15. The probe set according to claim 14 wherein each said detection group, D, of each electrophoretic probe has substantially the same spectral properties.

16. The probe set of claim 15 wherein said fluorescent molecule is selected from a group defined by the formula:

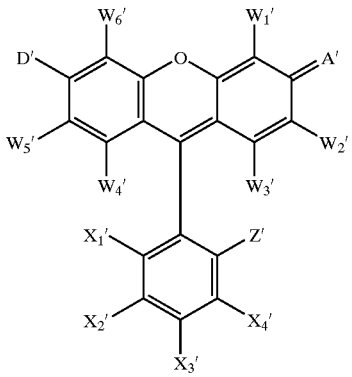

wherein:
Z' is COOH,
A' is O,
D' is OH, OR$^{3'}$ wherein R$^{3'}$ is lower alkyl, substituted lower alkyl, aryl, or substituted aryl,
W$^{1'}$, W$^{2'}$, W$^{3'}$, W$^{4'}$ and W$^{6'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, or imino,
W$^{5'}$ is H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, chlorine, fluorine, bromine, iodine, COOH, carboxylate, amide, nitrile, nitro, sulfonyl, sulfate, sulfone, amino, tethered amino, quaternary amino, or imino,
X$^{1'}$–X$^{4'}$ are independently H, lower alkyl, substituted lower alkyl, lower alkenyl, substituted lower alkenyl, lower alkynyl, substituted lower alkynyl, cycloalkyl, alkoxy, substituted alkoxy, phenoxy, substituted phenoxy, aromatic, substituted aromatic, phenyl, substituted phenyl, polycyclic aromatic, substituted polycyclic aromatic, heterocyclic, substituted heterocyclic, chlorine, fluorine, bromine, iodine, COOH, carboxylate, amide, nitrile, nitro, sulfonyl, sulfate, sulfone, amino, tethered amino, quaternary amino, or imino,
wherein W$^{2'}$ and W$^{3'}$ may be taken together to form one or more rings comprising 4 to 14 atoms and comprising 1 to 7 unsaturations, and
wherein W$^{4'}$ and W$^{5'}$ may be taken together to form a ring comprising 4 to 14 atoms and comprising 1 to 7 unsaturations.

17. The probe set of claim 15 wherein said fluorescent molecule is selected from the group defined by the formula:

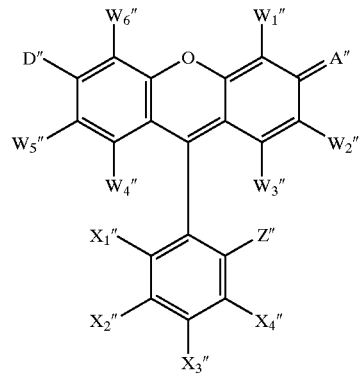

wherein
Z" is COOH,
A" is O, N(R$^{1"}$)(R$^{2"}$) wherein R$^{1"}$ and R$^{2"}$ are independently lower alkyl, or substituted lower alkyl,
D" is OH, OR$^{3"}$ wherein R$^{3"}$ is lower alkyl, substituted lower alkyl, aryl, or substituted aryl,
W$^{1"}$ and W$^{6"}$ are independently H, lower alkyl, substituted lower alkyl, COOH, chloro, or fluoro,
W$^{2"}$ and W$^{5"}$ are independently H, lower alkyl, substituted lower alkyl, COOH, chloro, or fluoro,
W$^{3"}$ and W$^{4"}$ are independently H, lower alkyl, substituted lower alkyl, COOH, chloro, or fluoro,
wherein W$^{2"}$ and W$^{3"}$ may be taken together to form one or more rings comprising 4 to 14 atoms and comprising 1 to 7 unsaturations, and
wherein W$^{4"}$ and W$^{5"}$ may be taken together to form a ring comprising 4 to 14 atoms and comprising 1 to 7 unsaturations,
X$^{1"}$–X$^{4"}$ are independently H, chloro, fluoro, COOH, bromo, or iodo.

18. The probe set of claim 17 wherein Z" is carboxyl, W$^{6"}$ and W$^{1"}$ are lower alkyl, W$^{5"}$ and W$^{2"}$ are halogen, X$^{2"}$ and X$^{3"}$ are hydrogen or carboxyl and X$^{1"}$ and X$^{4"}$ are hydrogen or halogen.

19. The probe set of claim 17 wherein Z" is carboxyl, W$^{6"}$ and W$^{1"}$ are methyl, W$^{5"}$ and W$^{2"}$ are chloro, one of X$^{2"}$ and are hydrogen and the other is carboxyl and X$^{1"}$ and X$^{4"}$ are hydrogen.

20. The probe set of claim 17 wherein Z" is carboxyl, W$^{6"}$ and W$^{1"}$ are methyl, W$^{5"}$ and W$^{2"}$ are chloro, one of X$^{2"}$ and X$^{3"}$ are hydrogen and the other is carboxyl and X$^{1"}$ and X$^{4"}$ are chloro.

* * * * *